(12) United States Patent
Kachanov et al.

(10) Patent No.: US 8,885,167 B2
(45) Date of Patent: *Nov. 11, 2014

(54) CAVITY ENHANCED LASER BASED GAS ANALYZER SYSTEMS AND METHODS

(71) Applicant: Li-Cor, Inc., Lincoln, NE (US)

(72) Inventors: Alexander Kachanov, San Jose, CA (US); Serguei Koulikov, Mountain View, CA (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/668,005

(22) Filed: Nov. 2, 2012

(65) Prior Publication Data

US 2014/0123729 A1    May 8, 2014

(51) Int. Cl.
*G01N 21/00* (2006.01)
*G01N 21/17* (2006.01)

(52) U.S. Cl.
CPC ..................................... *G01N 21/17* (2013.01)
USPC ........................................................ 356/437

(58) Field of Classification Search
CPC .......... G01N 21/8507; G01N 21/3504; G01N 21/3577; G01N 21/39; G01N 2291/021; G01J 3/42; G01J 3/30
USPC ................... 356/432–440, 409; 250/573, 576
See application file for complete search history.

(56) References Cited

U.S. PATENT DOCUMENTS

| | | |
|---|---|---|
| 3,938,365 A | 2/1976 | Dewey, Jr. |
| 4,793,709 A | 12/1988 | Jabr et al. |
| 5,432,610 A | 7/1995 | King et al. |
| 5,528,040 A | 6/1996 | Lehmann |
| 5,544,186 A | 8/1996 | Sauer et al. |
| 5,912,740 A | 6/1999 | Zare et al. |
| 5,929,981 A | 7/1999 | Keilbach |
| 5,973,864 A | 10/1999 | Lehmann et al. |
| 6,084,682 A | 7/2000 | Zare et al. |
| 6,233,052 B1 | 5/2001 | Zare et al. |

(Continued)

FOREIGN PATENT DOCUMENTS

| | | |
|---|---|---|
| JP | 07-270308 A | 10/1995 |
| WO | WO 2007/004168 A1 | 1/2007 |
| WO | WO 2008/026189 A1 | 3/2008 |

OTHER PUBLICATIONS

Burggraf et al., "Quantitative Photoacoustic Spectroscopy of Intensely Light-Scattering Thermally Thick Samples," Anal. Chem., 1981, vol. 53, pp. 759-764.

(Continued)

*Primary Examiner* — Hoa Pham
(74) *Attorney, Agent, or Firm* — Gerald T. Gray; Leydig, Voit & Mayer, LLP

(57) ABSTRACT

Cavity enhanced absorption spectroscopy systems and methods for detecting trace gases using a resonance optical cavity, which contains a gas mixture to be analyzed, and a laser coupled to the cavity by optical feedback. The cavity has any of a variety of configurations with two or more mirrors, including for example a linear cavity, a v-shaped cavity and a ring optical cavity. The cavity will have multiple cavity resonant modes, or a comb of frequencies spaced apart, as determined by the parameters of the cavity, including the length of the cavity, as is well known. Systems and methods herein also allow for optimization of the cavity modes excited during a scan and/or the repetition rate.

15 Claims, 14 Drawing Sheets

(56) References Cited

U.S. PATENT DOCUMENTS

| | | | |
|---|---|---|---|
| 6,466,322 | B1 | 10/2002 | Paldus et al. |
| 6,504,145 | B1 | 1/2003 | Romanini et al. |
| 6,608,683 | B1 | 8/2003 | Pilgrim et al. |
| 6,618,148 | B1 | 9/2003 | Pilgrim et al. |
| 7,012,696 | B2 | 3/2006 | Orr et al. |
| 7,069,769 | B2 | 7/2006 | Kung |
| 7,245,380 | B2 | 7/2007 | Kosterev |
| 7,259,856 | B2 | 8/2007 | Kachanov et al. |
| 7,263,871 | B2 | 9/2007 | Selker et al. |
| 7,398,672 | B2 | 7/2008 | Riddle |
| 7,450,240 | B2 | 11/2008 | Morville et al. |
| 7,535,573 | B2 | 5/2009 | Kachanov et al. |
| 7,569,823 | B2 | 8/2009 | Miller |
| 7,606,274 | B2 * | 10/2009 | Mirov et al. ............ 372/20 |
| 7,612,885 | B2 | 11/2009 | Cole et al. |
| 7,663,756 | B2 | 2/2010 | Cole |
| 7,679,750 | B2 | 3/2010 | Li et al. |
| 7,765,871 | B2 | 8/2010 | Riddle |
| 7,805,980 | B2 | 10/2010 | Kosterev |
| 7,902,534 | B2 | 3/2011 | Cole et al. |
| 2001/0003482 | A1* | 6/2001 | Zare et al. ............ 356/432 |
| 2003/0189711 | A1* | 10/2003 | Orr et al. ............ 356/484 |
| 2004/0065816 | A1 | 4/2004 | Ye et al. |
| 2006/0084180 | A1 | 4/2006 | Paldus et al. |
| 2006/0119851 | A1 | 6/2006 | Bounaix |
| 2006/0181710 | A1* | 8/2006 | Kachanov et al. ......... 356/437 |
| 2007/0195434 | A1* | 8/2007 | Koulikov et al. ......... 359/809 |
| 2008/0196477 | A1 | 8/2008 | Van Herpen |
| 2009/0185175 | A1* | 7/2009 | Cole et al. ............ 356/213 |
| 2009/0229345 | A1 | 9/2009 | Van Kesteren |
| 2009/0249861 | A1 | 10/2009 | Van Dijk et al. |
| 2009/0288474 | A1 | 11/2009 | Kalkman et al. |
| 2010/0002234 | A1 | 1/2010 | Cormier et al. |
| 2010/0011836 | A1 | 1/2010 | Kalkman et al. |
| 2010/0296095 | A1 | 11/2010 | Hong et al. |
| 2011/0214479 | A1 | 9/2011 | Kachanov et al. |
| 2011/0295140 | A1 | 12/2011 | Zaidi et al. |
| 2013/0044314 | A1 | 2/2013 | Koulikov et al. |
| 2013/0050706 | A1 | 2/2013 | Koulikov et al. |
| 2013/0083328 | A1* | 4/2013 | Koulikov et al. ......... 356/469 |

OTHER PUBLICATIONS

Cermak, Peter et al., "Optical-Feedback Cavity-Enhanced Absorption Spectroscopy Using a Short-Cavity Vertical-External-Cavity Surface-Emitting Laser," IEEE Photonics Technology Letters, IEEE Service Center, Piscataway, NJ, US, (2010), vol. 22, No. 21, pp. 1607-1609.

Clairon, A. et al., "Frequency Noise Analysis of Optically Self-Locked Diode Lasers," IEEE J. Quantum Electronics, 25(6):1131-1142 (1989).

Courtillot, I. et al., "Sub-ppb $NO_2$ detection by optical feedback cavity-enhanced absorption spectroscopy with a blue diode laser," Applied Physics B, (2006), vol. 85, No. 2-3, pp. 407-412.

Crosson, Eric R. et al., "Stable Isotope Ratios Using Cavity Ring-Down Spectroscopy: Determination of 13C/12C for Carbon Dioxide in Human Breath," Analytical Chemistry, May 1, 2002, vol. 74, No. 9, pp. 2003-2007.

Hamilton, D. J. et al., "A quantum cascade laser-based optical feedback cavity-enhanced absorption spectrometer for the simultaneous measurement of $CH_4$ and $N_2O$ in air," Applied Physics B, (2011), vol. 102, No. 4, pp. 879-890.

Hippler et al., "Cavity-enhanced resonant photoacoustic spectroscopy with optical feedback cw diode lasers: A novel technique for ultratrace gas analysis and high-resolution spectroscopy," The Journal of Chemical Physics, 2010, vol. 133, pp. 044308-1-044308-8.

Kosterev, A. A. et al., "Quartz-enhanced photoacoustic spectroscopy," Optics Letters 27(21):1902-1904 (Nov. 1, 2002).

Kosterev, A. A. et al., "Trace Humidity Sensor based on Quartz-Enhanced Photoacoustic Spectroscopy," LACSEA 2006, Incline Village, NV, Feb. 5-9 (2006).

Morville, J. et al., "Trace gas detection with DFB lasers and cavity ring-down spectroscopy," SPIE Proc., (2002), vol. 4485, pp. 236-243.

Morville, J. et al., "Effects of laser phase noise on the injection of a high-finesse cavity," Applied Optics, (2002), vol. 41, No. 33, pp. 6980-6990.

Morville, J. et al., "Two schemes for trace detection using cavity ringdown spectroscopy," Applied Physics B, (2004), vol. 78, pp. 465-476.

Morville, J. et al., "Fast, low-noise, mode-by-mode, cavity-enhanced absorption spectroscopy by diode-laser self-locking," Applied Physics B, (2005), vol. 80, No. 8, pp. 1027-1038.

Motto-Ros, V. et al., "Extensive characterization of optical feedback cavity enhanced absorption spectroscopy (OF-CEAS) technique: ringdown-time calibration of the absorption scale," Applied Physics B, (2008), vol. 91, No. 1, pp. 203-211.

Romanini, D. et al., "CW cavity ring down spectroscopy," Chemical Physics Letters, (1997), 264, pp. 316-322.

Romanini, D. et al., "Diode laser cavity ring down spectroscopy," Chemical Physics Letters, (1997), 270, pp. 538-545.

Romanini, D. et al., "Measurement of trace gases by diode laser cavity ringdown spectroscopy," Proc. SPIE EUROPTO (Ser. Environmental Sensing), (1999), vol. 3821, pp. 94-104.

Rossi, a. et al., "Optical enhancement of diode laser-photoacoustic trace gas detection by means of external Fabry-Perot cavity," Appl. Phys. Lett. 87, 041110 (2005).

Wehr, R. et al., "Optical feedback cavity-enhanced absorption spectroscopy for in situ measurements of the ratio 13C: 12C in $CO_2$," Applied Physics B, (2008), vol. 92, No. 3, pp. 459-465.

U.S. Appl. No. 12/667,995, filed Nov. 2, 2012.

European Search Report and Written Opinion for International Patent Application No. PCT/US2013/067612 issued Feb. 3, 2014.

* cited by examiner a)

b)

c)

CAVITY ENHANCED LASER BASED GAS ANALYZER SYSTEMS AND METHODS

BACKGROUND

The present invention relates generally to trace gas detection and more specifically to cavity enhanced absorption spectroscopy systems and methods for measuring trace gases.

A majority of present instruments capable of implementing cavity ring down absorption spectroscopy methods do not use, or are unable to effectively use, optical feedback to couple a laser to a cavity. This has consequences. For free decay rate cavity ring down spectroscopy (CRDS) methods, poor injection of the laser light to the cavity is achieved. As a result, the ring down rate is rather low (e.g., on the order of hundreds of Hertz). In the case of the phase shift cavity ring down absorption spectroscopy, the laser-cavity injection is also poor, causing additional noise in the measured signals. Also, for both decay rate and phase shift CRDS methods, the laser light coupled to the cavity has a complex frequency-phase characteristic, caused by a phase noise of the laser. The dynamic of the light emitted from the cavity is affected by interference between different frequency components of the light excited in the cavity. That causes an additional noise in the measurements.

Accordingly, there is a need for systems and methods for trace gas detection using a resonance optical cavity with improved performance, e.g., reduced noise and improved precision and accuracy, including cavity ring down spectroscopy systems and methods.

BRIEF SUMMARY

Embodiments herein provide systems and methods for trace gas detection using a resonance optical cavity. In certain embodiments, enhanced performance is achieved by using a laser coupled to the cavity by optical feedback (OF) as the cavity coupling rate is high and the frequency and phase of the intra-cavity light is well defined. For example, in certain embodiments, optical feedback is used to improve precision and accuracy of cavity enhanced laser based gas analyzers for detecting trace gases using phase shift cavity ring down absorption spectroscopy and/or free decay rate cavity ring down spectroscopy. In certain embodiments, the laser is coupled to the cavity by optical feedback even when the cavity is blocked from the laser. Certain embodiments herein also advantageously allow for enhanced control of the cavity modes excited.

The various embodiments described herein advantageously provide methods and apparatus for precise determination of trace gas concentrations with further improved stability and reproducibility as compared to existing devices and methods based upon various versions of cavity enhanced spectroscopy. The various embodiments advantageously provide higher immunity to variations of ambient conditions while retaining or improving other parameters such as the measurement repetition rate, measurement precision, low power consumption and low cost.

According to various embodiments, systems and methods are provided for detecting trace gases using a resonance optical cavity, which contains a gas mixture to be analyzed, and a laser coupled to the cavity by optical feedback. The cavity can have any of a variety of configurations with two or more mirrors, including for example a linear cavity, a v-shaped cavity and a ring optical cavity. The cavity will have multiple cavity resonant modes, or a comb of frequencies spaced apart, as determined by the parameters of the cavity, including the length of the cavity, as is well known. Said another way, the physical dimensions of the cavity define the FSR (free spectral range) of the cavity. In certain embodiments, one or two optical intensity modulators are placed between the laser and the cavity. Radiation (light) output from the laser, which is capable of being frequency scanned, is coupled to the cavity though one of the cavity mirrors (input mirror or cavity coupling mirror). The light emerging from the cavity though one of the cavity mirrors (output mirror) is coupled back to the laser. Input and output mirrors can be the same or different mirrors. In certain aspects, an optical attenuator or a partial optical isolator is placed between the laser and the cavity to provide optimal intensity control of the feedback light coupled to the laser. By changing the optical path length between the laser and the cavity, a phase of the optical feedback can be adjusted. In certain aspects, the phase of the optical feedback is controlled by a phasor (electro-optic modulator that imposes a modulation on the phase of the light) or other phase adjustment element. The intra-cavity optical power is monitored by a detector, e.g., photo-detector. The intensity of the light incident on the cavity can be monitored by another detector, e.g., photo-detector.

In one embodiment, to measure the cavity loss at different wavelengths, the frequency of the laser is scanned. When the frequency of the laser light is close to the frequency of one of the cavity transverse modes, the laser locks to the cavity mode due to the optical feedback effect as is well known. When the laser is locked to the cavity, and the laser frequency is close to the center of the cavity mode, the laser scanning is stopped, and a modulator, which is located between the laser and the input mirror of the cavity, starts to modulate the laser beam intensity. Depending on the amplitude and shape of the modulation signal, the time dependence of the light emitted from the cavity can be analyzed by different methods, for example: 1) measurements based on phase shift cavity ring down absorption spectroscopy, and 2) measurements based on free decay rate cavity ring down spectroscopy. In both methods, the optical cavity acts as a long pass filter with a time constant defined by the cavity round trip loss and the cavity length, and both methods are able to measure this time constant. Both of these methods are also not sensitive to the laser intensity. After the cavity loss has been measured at one cavity mode, the laser frequency is tuned to another frequency mode, and this is repeated until all necessary spectral information is obtained. The free decay rate cavity ring down spectroscopy method requires that the cavity is blocked from the laser during free decay rate measurements. In the case of using a single modulator, during the free decay period, the laser is also blocked from the cavity, i.e., no optical feedback is provided to laser, which might cause loss of the laser locking to the cavity. In one embodiment, when the input and output mirrors are different mirrors, the light emitted from the output mirror is coupled back to the laser so that the laser can continue to be locked to the cavity, while the cavity is blocked from the laser. In certain aspects, the feedback intensity is stabilized by using a second modulator, which advantageously minimizes the disturbance of the laser due to modulation of the laser beam.

One embodiment of an instrument based on the free decay rate cavity ring down spectroscopy method includes a laser, an optical cavity, a phasor (or other phase control element), and a photo-detector. In certain aspects, the instrument includes an attenuator to control the intensity of the optical feedback. However, in one embodiment, a separate modulator is not included. The laser is periodically turned on and off by modulation of the laser diode current. After the laser is turned on, its frequency tunes to the equilibrium value. When the output laser frequency is close to the cavity mode, the laser locks to the cavity mode. When the laser frequency reaches the center, or near the center, of the desirable cavity mode, the laser is turned off, and the decay of the intra-cavity power is measured. In certain aspects, the shape of laser diode current modulation is optimized to maximize the repetition rate. The laser diode current in the "off" state is below the laser threshold, but it can be non-zero. In certain aspects, the phase of the optical feedback is stabilized by periodic measurements of the time dependence of the intra-cavity power while the laser is scanned through a cavity mode, or by other methods. Because the cavity is not completely blocked from the laser, when the laser is off, the laser and the cavity create a system of two coupled cavities. In that case, the decay time in the optical cavity not only depends on the intra-cavity loss, but also depends on the coupling between two cavities. However, because the optical length of both cavities is fixed (the laser-cavity optical path is controlled by the phasor), the frequencies of the cavities are also fixed. Hence, the shot-to-shot performance is not affected by incomplete blocking of the laser from the cavity, if the phase of the optical feedback is controlled. Additional spectral fringes caused by interference of an optical element placed between the laser and the cavity can be measured by periodic measurement of the cavity loss without absorbing species present in the cavity.

In one embodiment, the shape of the applied laser diode current is chosen to actively select one or more particular cavity modes and the order that cavity modes are excited and locked on. For example, the shape of the applied laser diode current can be optimized or chosen to excite cavity modes in any random (controlled) order during an excitation cycle, e.g., to allow for measuring dynamics of the intracavity optical power for desired cavity modes, such as measuring the ring down decay for one particular cavity mode, for a continuous set of cavity modes, or for a preselected set of the cavity modes. The order of the cavity modes excited within a set of modes during an excitation cycle can be sequential, with all modes locked on, or it can be sequential with certain modes skipped, or the order can be non-sequential. The shape of the laser current can be chosen to measure ring down decay once or multiple times per cycle for a particular cavity mode, depending on the importance of that mode in the spectral analysis being conducted.

In one embodiment, to analyze multiple species in the gas mixture being analyzed, more than one laser is coupled to the cavity separately or simultaneously, e.g., using beam splitting elements, dichroic mirrors, rotating mirrors and/or dispersive components or elements as are well known. The intra-cavity optical power and decay is detected or measured using one or multiple photodiodes, e.g., multiple photodiodes, each optimized for detection at a specific wavelength or wavelength range. Different lasers can operate sequentially or simultaneously.

Advantageously, different detection methodologies can be used in the same instrument. For example both phase shift cavity ring down spectroscopy and free decay rate cavity ring down spectroscopy can be used in the same instrument. Additionally, cavity enhanced direct absorption methodologies can be used in the same instrument. The various methodologies can be used to make measurements in the same excitation cycle(s) or in different cycles.

According to one embodiment, a method is provided for measuring cavity loss of a resonant optical cavity over a range of frequencies by exciting one or a plurality of cavity modes of the cavity in a controlled manner, the cavity having at least two cavity mirrors, one of which is a cavity coupling mirror, using a laser that emits continuous wave laser light, the laser being responsive to optical feedback light emerging from the cavity, wherein a mean optical frequency of the laser is adjustable over a range of frequencies. The method typically includes coupling the laser light to the cavity via the cavity coupling mirror using mode matching optics, the cavity having a plurality of optical resonance cavity modes that have frequencies within said range of frequencies of the laser, and applying to the laser a current having a predetermined current profile so as to adjust the mean optical frequency of the laser and so as to excite cavity modes in an excitation order responsive to a shape of the applied current profile, said excitation order comprising excitation of a single desired cavity mode two or more consecutive times and/or excitation of multiple desired cavity modes in a non-consecutive order. The method also typically includes detecting dynamics of the intra cavity optical power of light circulating in the cavity after a cavity mode has been excited. In certain aspects, detecting dynamics include measuring a free decay cavity ring down rate or measuring a phase shift of the intracavity optical power of light, or both measuring a free decay rate and a phase shift. In certain aspects, the mode(s) excited are excited in a sequential order, or in a non-sequential order during an excitation cycle. In certain aspects, the shape of the applied current profile is controlled such that one or more modes are skipped intentionally. In certain aspects, detecting dynamics includes isolating the cavity from the laser wherein the laser light is interrupted from interacting with or influencing the cavity while maintaining optical feedback between the laser and light emerging from the cavity. In certain aspects, the phase of the optical feedback is controlled using a phase adjustment element positioned along an optical path between the laser and the mirror from which the optical feedback light emerges. In certain aspects, the intensity of the laser light impinging on the cavity is modulated using a modulation element. When light emerging from a cavity mirror other than the cavity coupling mirror is used for optical feedback, a second modulation element is used in certain aspects to stabilize the intensity of feedback light interacting with the laser. In certain aspects, the applied current profile is optimized to increase the repetition rate, e.g., decrease a time between two (or more) measuring events, during an excitation cycle. In certain aspects, detecting dynamics of the intra cavity optical power includes setting a laser current below the laser threshold value or turning the laser off, wherein the laser current profile includes a compensation pulse portion at or near the maximum laser driving current for a time period sufficient to compensate for some or all of the laser heat lost while the laser current was below the laser threshold value or off. In certain aspects, the method includes determining a concentration of a gas in the cavity responsive to detecting dynamics of the intra cavity optical power.

According to another embodiment, a system is provided for measuring cavity loss of a resonant optical cavity over a range of frequencies by exciting one or a plurality of cavity modes of the cavity. The system typically includes a resonant optical cavity having at least two cavity mirrors, one of which is a cavity coupling mirror, the cavity having a plurality of optical resonance cavity modes, and a laser that emits continuous wave laser light, wherein the laser is capable of being scanned whereby a mean optical frequency of the laser is adjustable over a range of frequencies, and wherein the laser is responsive to optical feedback light emerging from the cavity, and wherein the modes of the cavity have frequencies within said range of frequencies of the laser. The system also typically includes mode matching optics configured to couple the laser light to the cavity via the cavity coupling mirror, and a control module coupled with the laser and adapted to apply a current having a predetermined current profile to the laser so as to adjust the mean optical frequency of the laser and to excite cavity modes in an excitation order responsive to a shape of the applied current profile, said excitation order comprising excitation of a single desired cavity mode two or more consecutive times and/or excitation of multiple desired cavity modes in a non-consecutive order. The system also typically includes a first detector configured to measure dynamics of the intra cavity optical power of light circulating in the cavity after a cavity mode has been excited. In certain aspects, the dynamics detected include a measurement of a free decay cavity ring down rate or a measurement of a phase shift of the intracavity optical power of light, or both a measurement of a free decay rate and measurement of a phase shift. In certain aspects, the mode(s) excited are excited in a sequential order, or in a non-sequential order. In certain aspects, the shape of the applied current profile is controlled such that one or more modes are skipped intentionally. In certain aspects, the detector measures dynamics while the cavity is isolated from the laser, e.g., using a modulation element or other element, wherein the laser light is interrupted from interacting with or influencing the cavity while maintaining optical feedback between the laser and light emerging from the cavity. In certain aspects, the system includes a phase adjustment element positioned along an optical path between the laser and the mirror from which the optical feedback light emerges to control the phase of the optical feedback light interacting with the laser. In certain aspects, a modulation element is included to modulate the intensity of the laser light impinging on the cavity. When light emerging from a cavity mirror other than the cavity coupling mirror is used for optical feedback, a second modulation element is included in certain aspects to stabilize the intensity of feedback light interacting with the laser. In certain aspects, the applied current profile is optimized by the control module to increase the repetition rate, e.g., decrease a time between two (or more) measuring events, during an excitation cycle. In certain aspects, dynamics of the intra cavity optical power are detected by setting a laser current below the laser threshold value, or turning the laser off, wherein the laser current profile includes a compensation pulse portion at or near the maximum laser driving current for a time period sufficient to compensate for some or all of the laser heat lost while the laser current was below the laser threshold value or off. In certain aspects, the system includes a processor adapted to determine a concentration of a gas in the cavity responsive to a signal received from the first detector.

According to another embodiment, a gas analyzer is provided for detecting or measuring one or more analyte species present in a gaseous or liquid medium. The gas analyzer typically includes a resonant optical cavity containing said medium and having at least two cavity mirrors, one of which is a cavity coupling mirror, the cavity having a plurality of optical resonance cavity modes, and a laser that emits continuous wave laser light, wherein the laser is capable of being scanned whereby a mean optical frequency of the laser is adjustable over a range of frequencies, and wherein the laser is responsive to optical feedback light emerging from the cavity, and wherein the modes of the cavity have frequencies within said range of frequencies of the laser. The gas analyzer also typically includes mode matching optics configured to couple the laser light to the cavity via the cavity coupling mirror, and a control module coupled with the laser and adapted to apply a current having a predetermined current profile to the laser so as to adjust the mean optical frequency of the laser and to excite cavity modes in an excitation order responsive to a shape of the applied current profile, said excitation order comprising excitation of a single desired cavity mode two or more consecutive times and/or excitation of multiple desired cavity modes in a non-consecutive order. The gas analyzer also typically includes a first detector configured to measure, and to generate a signal representing, dynamics of the intra cavity optical power of light circulating in the cavity after a cavity mode has been excited. In certain aspects, the dynamics detected or measured include a measurement of a free decay cavity ring down rate or a measurement of a phase shift of the intracavity optical power of light, or both a measurement of a free decay rate and measurement of a phase shift. In certain aspects, the mode(s) excited are excited in a sequential order, or in a non-sequential order. In certain aspects, the shape of the applied current profile is controlled such that one or more modes are skipped intentionally. In certain aspects, the detector measures dynamics while the cavity is isolated from the laser, e.g., using a modulation element or other element, wherein the laser light is interrupted from interacting with or influencing the cavity while maintaining optical feedback between the laser and light emerging from the cavity. In certain aspects, the system includes a phase adjustment element positioned along an optical path between the laser and the mirror from which the optical feedback light emerges to control the phase of the optical feedback light interacting with the laser. In certain aspects, a modulation element is included to modulate the intensity of the laser light impinging on the cavity. When light emerging from a cavity mirror other than the cavity coupling mirror is used for optical feedback, a second modulation element is included in certain aspects to stabilize the intensity of feedback light interacting with the laser. In certain aspects, the applied current profile is optimized by the control module to increase the repetition rate, e.g., decrease a time between two (or more) measuring events, during an excitation cycle. In certain aspects, dynamics of the intra cavity optical power are detected by setting a laser current below the laser threshold value, or turning the laser off, wherein the laser current profile includes a compensation pulse portion at or near the maximum laser driving current for a time period sufficient to compensate for some or all of the laser heat lost while the laser current was below the laser threshold value or off.

According to yet another embodiment, a method is provided for measuring cavity loss of a resonant optical cavity over a range of frequencies by exciting one or a plurality of cavity modes of the cavity in a controlled manner, the cavity having at least two cavity mirrors, one of which is a cavity coupling mirror, using a laser that emits continuous wave laser light, wherein the laser is responsive to optical feedback light emerging from the cavity, and wherein a mean optical frequency of the laser is adjustable over a range of frequencies. The method typically includes coupling the laser light to the cavity via the cavity coupling mirror using mode matching optics, the cavity having a plurality of optical resonance cavity modes that have frequencies within said range of frequencies of the laser, and applying to the laser a drive current comprising a series of current pulses, each having a predetermined current profile, so as to adjust the mean optical frequency of the laser and to excite desired cavity modes in an order as determined based on the shape of the applied current pulses, wherein an end portion of one current pulse sets the laser drive current below the a laser threshold value, and wherein the current profile of the next current pulse applied to the laser includes a compensation pulse portion that drives the laser at or near a maximum laser driving current for a duration that sufficient to compensates for some or all of the laser heat lost while the laser drive current was below the laser threshold value and to excite the next mode in said order. The method also typically includes detecting dynamics of the intra cavity optical power of light circulating in the cavity after a cavity mode has been excited.

According to still a further embodiment, a system is provided for measuring cavity loss of a resonant optical cavity over a range of frequencies by exciting one or a plurality of cavity modes of the cavity. The system typically includes a resonant optical cavity having at least two cavity mirrors, one of which is a cavity coupling mirror, the cavity having a plurality of optical resonance cavity modes, a laser that emits continuous wave laser light, wherein the laser is capable of being scanned whereby a mean optical frequency of the laser is adjustable over a range of frequencies, and wherein the laser is responsive to optical feedback light emerging from the cavity, and wherein the modes of the cavity have frequencies within said range of frequencies of the laser, and mode matching optics configured to couple the laser light to the cavity via the cavity coupling mirror. The system also typically includes a control module coupled with the laser and adapted to apply a drive current comprising a series of current pulses, each pulse having a predetermined current profile, to the laser so as to adjust the mean optical frequency of the laser and to excite desired cavity modes in an excitation order as determined based on the shape of the applied current pulses; and a first detector configured to measure dynamics of the intra cavity optical power of light circulating in the cavity after a cavity mode has been excited, wherein an end portion of one current pulse sets the laser drive current below a laser threshold value, and wherein the current profile of the next current pulse applied to the laser includes a compensation pulse portion that drives the laser at or near a maximum laser driving current a current level and for a duration that sufficient to compensates for some or all of the laser heat lost while the laser current was below the laser threshold value and to excite the next mode in said excitation order.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIGS. 1-3 show configurations using a V-shaped cavity; FIGS. 4 and 5 show configurations using a linear, two-mirror cavity; and FIGS. 6 and 7 show configurations using a ring cavity.

DETAILED DESCRIPTION

According to various embodiments, cavity enhanced absorption spectroscopy systems and methods are provided for detecting trace gases using a resonance optical cavity, which contains a gas mixture to be analyzed, and a laser coupled to the cavity by optical feedback. The cavity can have any of a variety of configurations with two or more mirrors, including for example a linear cavity, a v-shaped cavity and a ring optical cavity. The cavity will have multiple cavity resonant modes, or a comb of frequencies spaced apart, as determined by the parameters of the cavity, including the length of the cavity, as is well known.

System Configurations

Figure 1:
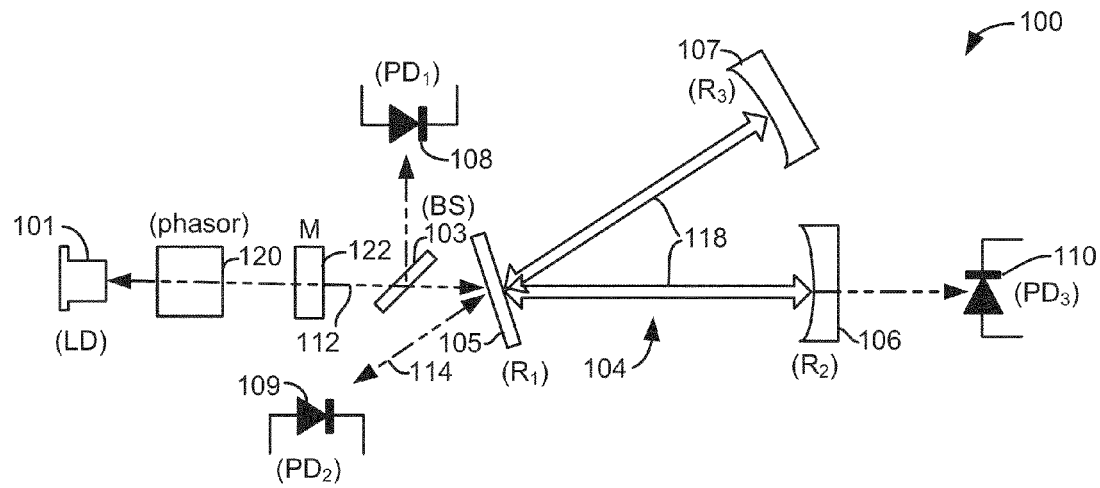
FIGS. 1-7 illustrate examples of useful configurations according to various embodiments.
Figure 8:
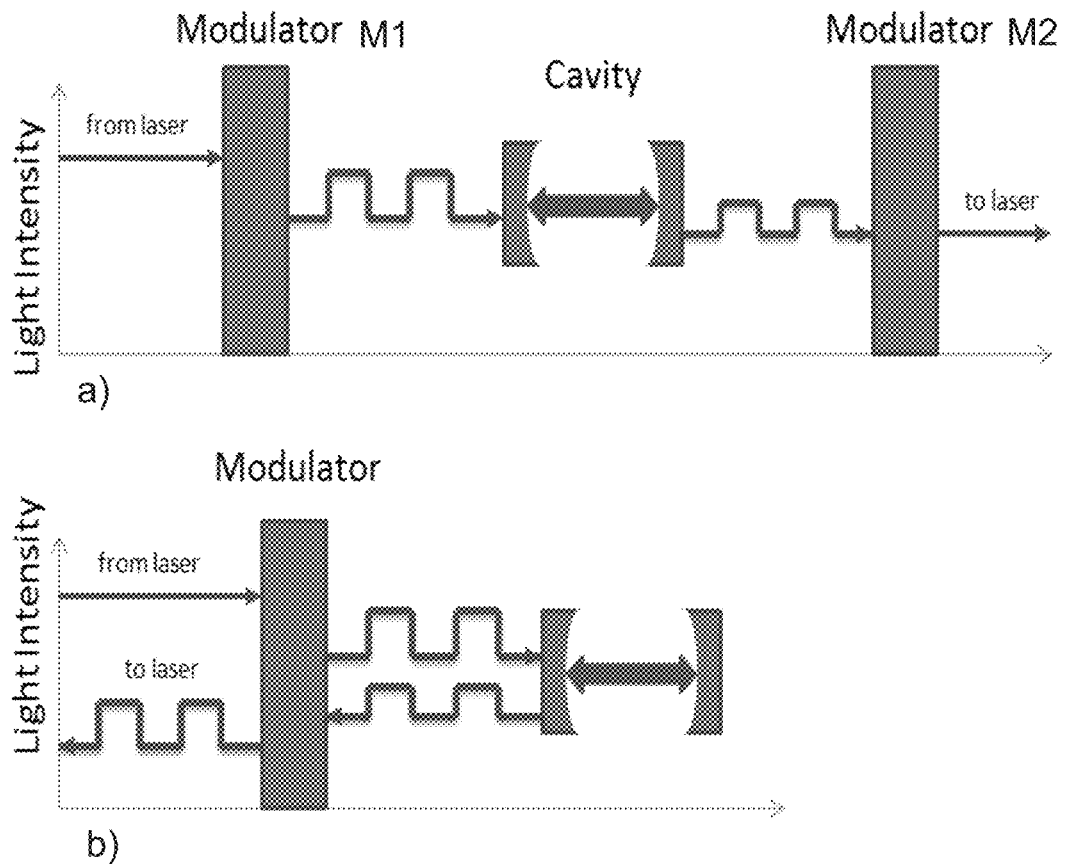
FIG. 8 shows one- and two-modulator configurations according to various embodiments. When a single modulator is used, the feedback intensity is also modulated.

FIG. 1 illustrates a cavity enhanced absorption spectroscopy (CEAS) system 100 according to one embodiment. As shown, CEAS system 100 includes a light source 101 that emits continuous wave coherent light, such as continuous wave laser light, an optical cavity 104 and three detectors (108, 109 and 110). As shown, cavity 104 is a V-shaped cavity defined by cavity coupling mirror 105 and mirrors 106 and 107. In certain aspects, an enclosure or housing (not shown) is present to provide an air tight seal for cavity 104 such as to allow control of the environment within the housing and hence the cavity 104. Environmental control might include control of the temperature, the pressure and/or the flow rate of the medium (gaseous or liquid) into and out of a cell enclosing cavity 104. One or more optical components (not shown, e.g., mode matching optical component(s)) are configured and arranged to facilitate directing laser light from source 101 to the optical cavity 104 via cavity coupling mirror 105. In the embodiment shown in FIG. 1, a beam splitting element 103 is positioned and aligned so as to allow substantially all of the incident light 112 emitted or generated by source 101 to impinge on cavity coupling mirror 105. A small portion of the incident light beam 112 is directed (e.g., reflected or refracted) by element 103 to detector 108. Cavity coupling mirror 105, in this embodiment, is arranged at an angle with respect to beam 112 such that a portion of incident light 112 is reflected off of mirror 105 as reflected beam 114 and detected by detector 109. A portion of incident light 112 enters cavity 104 via mirror 105. Depending on the frequency of incident light 112 and the optical length of cavity 104 (e.g., optical length from mirror 107 to mirror 105 to mirror 106), light 118 circulating in the cavity may build up and resonate at one or a plurality of cavity modes. A portion of the intracavity light 118 circulating in cavity 104 between mirror 107, 105 and 106, emerges or escapes via mirror 106 and is detected by detector 110. Alternately, light escaping from mirror 107 can be detected or light escaping from mirror 105 can be detected, e.g., light escaping from mirror 105 impinges on element 103, which directs a portion to a detector (not shown) positioned below element 103 in FIG. 1. In any case, beamsplitter 103 allows a portion of the light escaping mirror 105 along the incident light beam path to pass back to source 101, e.g., for optical feedback. Light returning to source 101 passes through a phasor 120 (e.g., an electro-optic modulator that imposes a modulation on the phase of the light), which advantageously provides for phase control of the optical feedback provided to source 101 from cavity 104. Optional modulator 122 can be provided to modulate the intensity of light travelling to and from source 101, e.g., in a double-pass configuration as shown in FIG. 8b.

Figure 9:
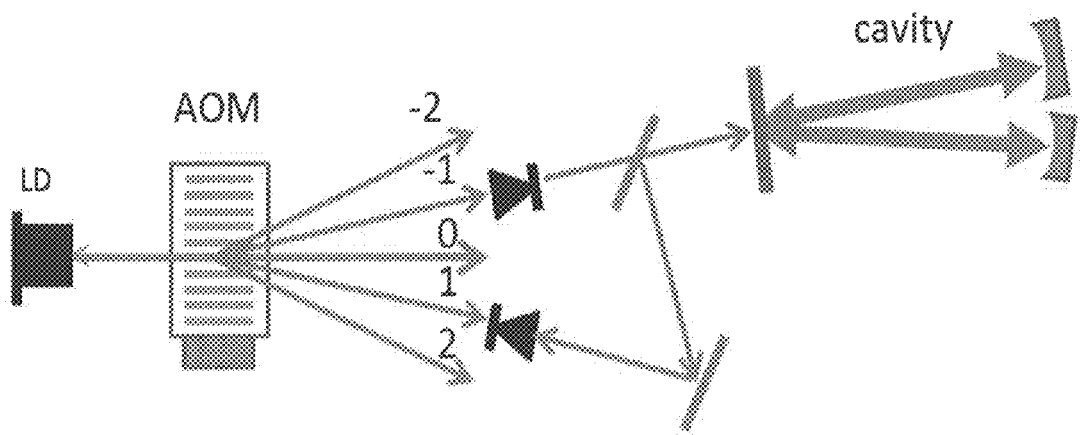
FIGS. 9-10 shows embodiments of an AOM used in two different double-pass configurations.
Figure 10:
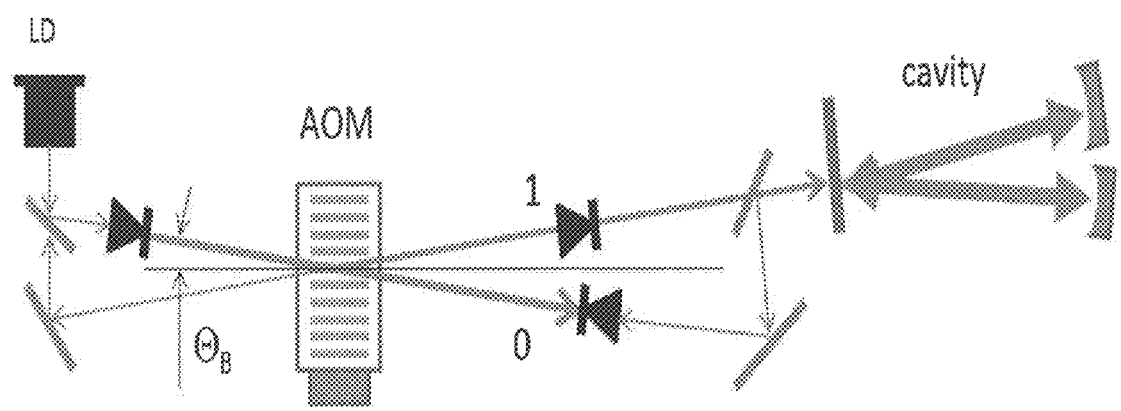

Any of a variety of modulators can be used. Examples of useful intensity modulators include electro-optic modulators (EOMs), acousto-optic modulators (AGMs), semiconductor optical amplifiers (SOAs) and variable optical attenuators (VOAs). Any other modulators can be used. Depending on the application, an acousto-optic modulator can be used in two configurations: when the modulated light beam has the same frequency or when the modulated beam has a shifted frequency. The first configuration shown in FIG. 9 works well for the phase shift cavity ring down absorption spectroscopy method, and the second configuration works well for both the phase shift cavity ring down absorption spectroscopy and the free decay rate cavity ring down spectroscopy methods. Only frequency shifted modulation provides acceptable contrast for the free decay rate cavity ring down spectroscopy method. The preferable condition is when the cavity is completely blocked from the laser when the intra-cavity power decay is measured. However, if the modulated light, incident on to the cavity, is frequency shifted, the light emitted from the cavity has also to be shifted back to the original frequency before it reaches the laser. This frequency shifting can be done using a second AOM or by double passing though the first AOM. FIGS. 9-10, discussed in more detail below, show an AOM used in double-pass configurations.

In certain aspects, source 101 includes a laser or other coherent light source that is sensitive or responsive to optical feedback and that emits radiation at the desired wavelength(s) or desired wavelength range(s). One useful laser is a semiconductor diode laser that is sensitive to optical feedback from light impinging on the laser from the cavity coupling mirror 105. Other laser sources might include diode lasers, quantum cascade lasers and solid state lasers. The reflectivities of mirrors 105, 106 and 107 define the optical feedback intensity. U.S. patent application Ser. No. 13/252,915, filed Oct. 14, 2011, which is incorporated herein by reference in its entirety, discloses laser based cavity enhanced spectroscopy systems including mirror optimization techniques. In one embodiment, source 101 is capable of being frequency scanned, whereby a mean optical frequency of the source is adjustable over a range of frequencies in a controlled manner. In the case of a laser, for example, this can be accomplished as is well known, such as, for example, by adjusting the current applied to a diode laser and/or adjusting a temperature of the laser medium. In certain aspects, the cavity 104 is also capable of being frequency scanned, e.g., by changing or adjusting an optical length of the cavity, whereby an optical frequency of a cavity resonance peak is adjustable over a range of frequencies. Adjustment of the optical length of the cavity can include adjusting or modulating a relative position of one or more of the cavity mirrors (e.g., using a piezo element coupled with one of the mirrors), adjusting a pressure of the medium within cavity 104 or using other methods as are known to one skilled in the art. An intelligence module or control module, such as a computer system, processor, ASIC or other control circuitry, is provided to enable automated control of the source frequency scan and/or cavity optical length adjustment.

In certain embodiments, each detector element (108, 109 and 110) includes a photodetector, such as a photodiode, and associated electronics, for detecting light and outputting a signal representing the detected light. Examples of useful photodetectors might include silicon, InGaAs, Ge or GAP based photodetectors. Other useful detectors include CCDs, photomultipliers, APD's, etc. An intelligence module (e.g., a computer system, processor, ASIC or other control circuitry; not shown) receives the detector output signals and processes these signals to produce or generate a signal that characterizes the cavity loss based on the detection methodology used, e.g., free decay rate, phase shift, direct absorption, etc. For example, U.S. patent application Ser. No. 13/218,359, filed Aug. 25, 2011, which is incorporated herein by reference in its entirety, discloses laser based cavity enhanced spectroscopy systems including techniques for producing normalized signals that are a linear function of total cavity loss and that are not sensitive to laser-cavity coupling.

In certain embodiments, CEAS system 100 is useful for detecting trace gases within a gas mixture present in the cavity 104. When the frequency of the light 112 emitted by source 101 approaches the frequency of one of the cavity modes, the light 112 entering the cavity 104 begins to fill the cavity to that mode and may lock to that cavity mode. The optical intensity of the light 118 circulating inside the resonance cavity reflects total cavity loss at the moment when the light frequency of light 112 coincides with the cavity mode transmission peak. The total cavity loss is a sum of the cavity mirror losses and losses caused by absorption by the medium present in the cavity, e.g., absorption caused by absorbing analyte species present in the gaseous or liquid medium in cavity 104. Examples of such species detectable by embodiments herein include $H_2O$, $CO_2$, $CH_4$, $CO$, $HF$, $HCl$, $C_2H_6$, $C_2H_4$, $C_2H_2$, $N_2O$, $H_2O_2$, $NH_2$ and many others.

Figure 2:
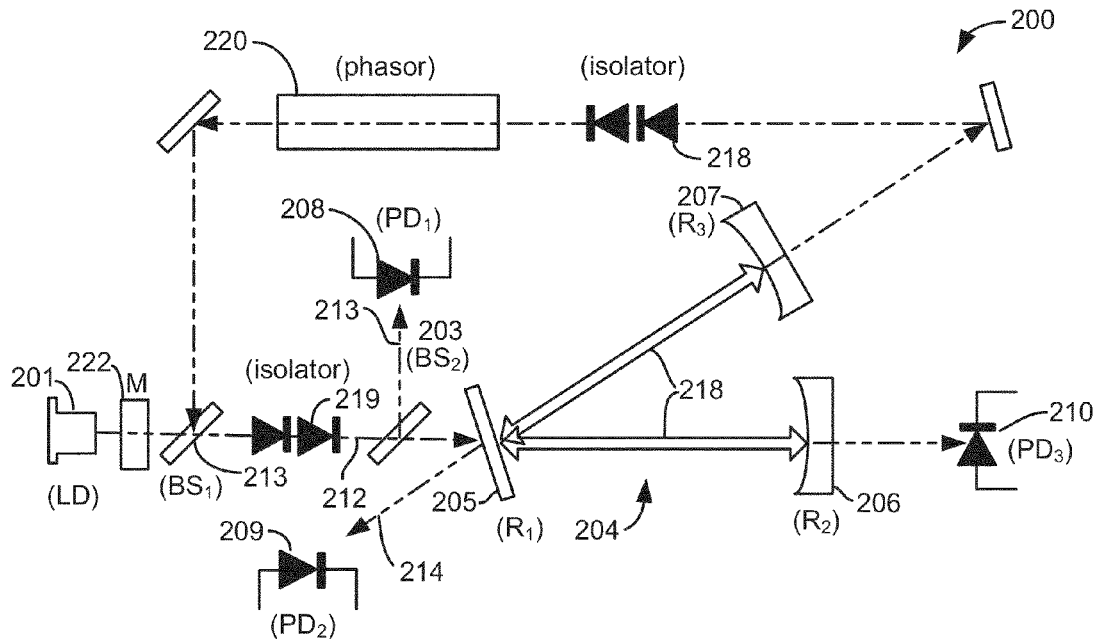

FIG. 2 illustrates a cavity enhanced absorption spectroscopy (CEAS) system 200 according to another embodiment. The principle of operation of CEAS system 200 is similar to that of CEAS system 100, for example, including a v-shaped cavity structure 204, with cavity mirror 205 being a cavity coupling mirror. Cavity coupling mirror 205 is positioned such that incident light beam 212 generated by laser diode source 201 impinges upon mirror 205 at an angle relative to the plane defined by mirror 205 at the area of impact so that light is reflected to photodetector 209. Beamsplitting element 203 directs a portion 213 of incident beam 212 to detector 208. Photodetector 210, in this embodiment, is positioned to receive and detect the portion of the intra-cavity light 218 circulating back and forth within cavity 204 between mirrors 805, 806 and 807 that emerges or escapes via mirror 206. Similar to the operation of CEAS 100, photodetector 208 detects and generates a signal representing the intensity of the laser light 212 incident on the cavity coupling mirror 205, detector 209 detects and generates a signal representing the intensity of the laser light 214 reflected by the cavity coupling mirror 205, and detector 210 detects and generates a signal representing the intracavity optical power of light circulating in the cavity 204. An intelligence module, such as a computer system, processor, ASIC or other control circuitry, receives the detector output signals and processes these signals to produce or generate a signal that characterizes the cavity loss based on the detection methodology used.

Also shown in FIG. 2 are additional elements to enhance control of the optical feedback, specifically control of the optical feedback to source 201. As shown, light emerging from cavity mirror 207 passes through a phasor 220 (or other adjustable light attenuating element) and returns to source 201, via beamsplitting element 213. Optical isolators 218 and 219 are provided to completely block light which travels in the opposite direction. For example, optical isolator element 819 blocks light returning (e.g., reflected light or light escaping from the cavity via mirror 205) from mirror 205 toward source 201, and optical isolator element 218 prevents light returning from phasor 220 (e.g., light reflected by phasor 220 or source light reflected by beamsplitter 213 that is passing through phasor 220 on an opposite path) from impinging on mirror 207. Selection of the cavity mirror reflectivities (e.g., $R_1$, $R_2$ and $R_3$) helps define the optical feedback intensity provided to source 201. Use of phasor 220 advantageously allows for phase control of the optical feedback provided to source 201 from the cavity 204. Optional modulator 222 can be provided to modulate the intensity of light travelling to and from source 201, e.g., in a double-pass configuration as shown in FIG. 8b.

Figure 3:
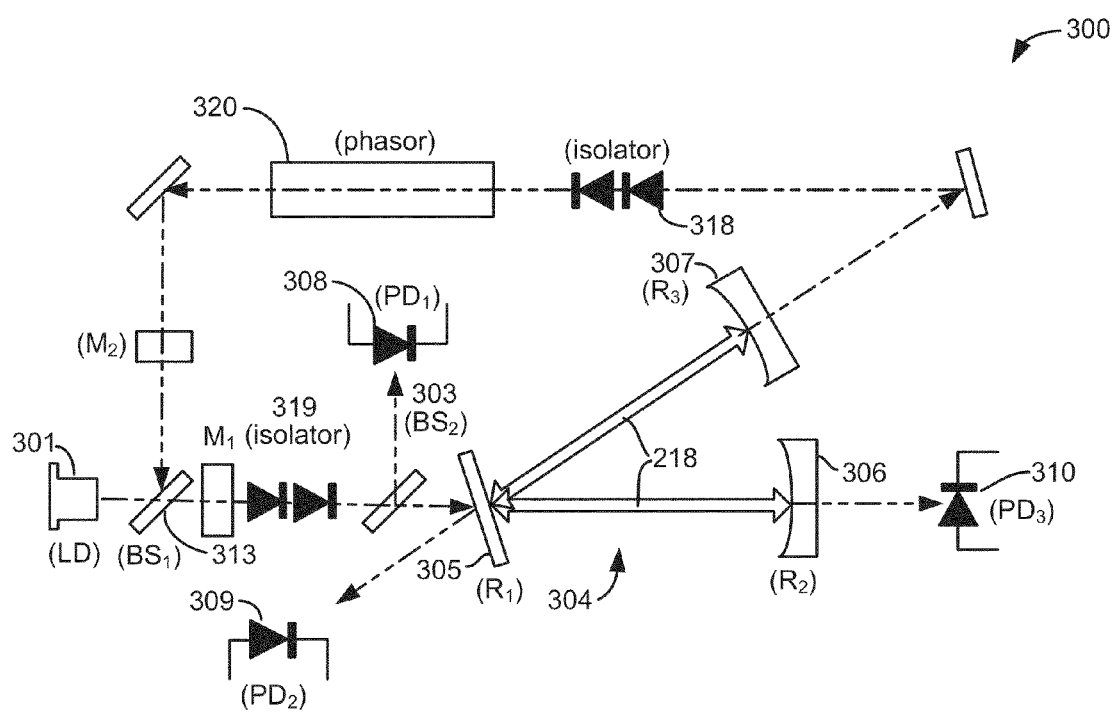

The configuration shown in FIG. 3 is similar to that shown in FIG. 2, but includes a two modulator configuration including modulator $M_1$ and modulator $M_2$. The two modulator configuration is used to stabilize the feedback intensity and reduce any laser disturbance due to modulation as shown in FIG. 8a; modulator $M_1$ modulates the source light impinging on the cavity 304 and modulator $M_2$ (de)modulates the light emerging from the cavity 304 and incident on the laser source 301.

Figure 4:
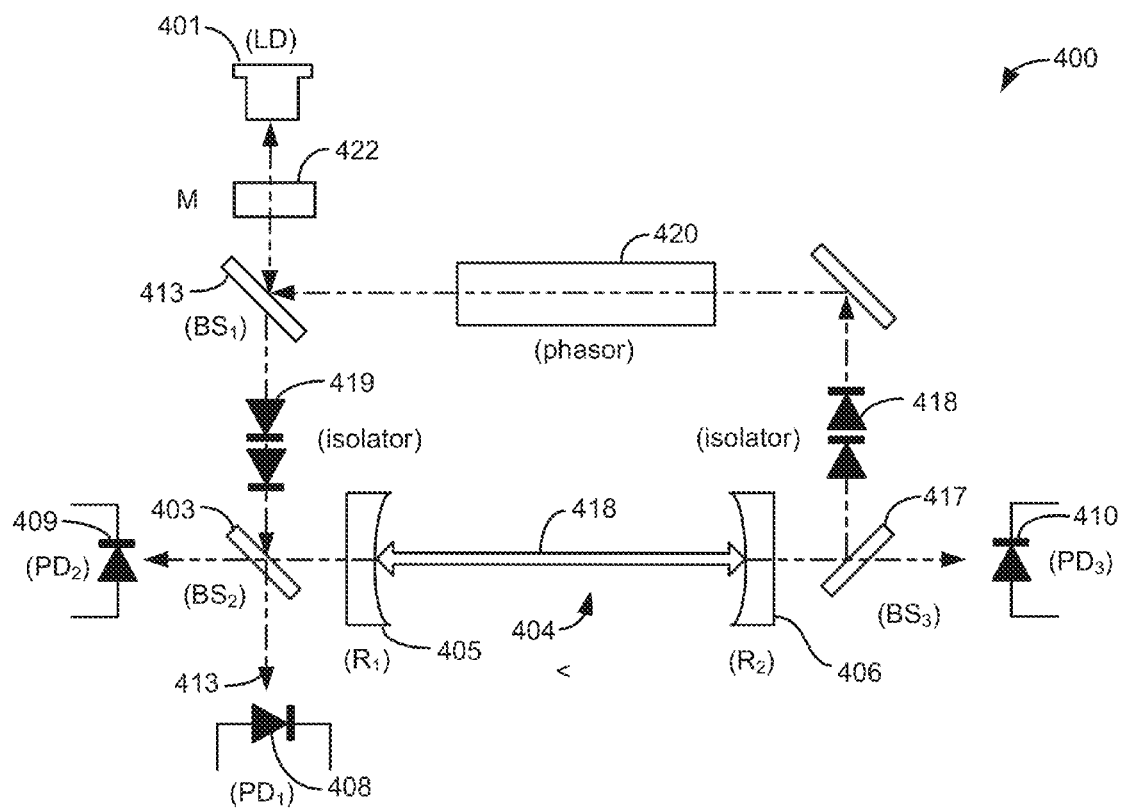

FIG. 4 illustrates a cavity enhanced absorption spectroscopy (CEAS) system 400 according to yet another embodiment. The principle of operation of CEAS system 400 is similar to that of CEAS system 100, for example, but includes a two-mirror linear cavity structure 404, with cavity mirror 405 being a cavity coupling mirror. Cavity coupling mirror 405 is positioned such that incident light beam 412 generated by laser diode source 401 impinges upon mirror 405 perpendicular to the plane defined by mirror 405 at the area of impact so that light is reflected to photodetector 409 (through beamsplitter 403). Beamsplitting element 403 allows a portion 413 of incident beam 412 to pass to detector 408 and reflects the remainder to mirror 405. Photodetector 410, in this embodiment, is positioned to receive and detect the portion of the intra-cavity light 418 circulating within cavity 404 between mirrors 405 and 406 that emerges or escapes via mirror 406. Similar to the operation of CEAS 100, photodetector 408 detects and generates a signal representing the intensity of the laser light 412 incident on the cavity coupling mirror 405, detector 409 detects and generates a signal representing the intensity of the laser light reflected by the cavity coupling mirror 405, and detector 410 detects and generates a signal representing the intra-cavity optical power of light circulating in the cavity 404. An intelligence module (not shown) receives the detector output signals and processes these signals to produce or generate a signal that characterizes the cavity loss based on the detection methodology used.

Also shown in FIG. 4 are additional elements to enhance control of the optical feedback, specifically control of the optical feedback to source 401. As shown, a portion of light emerging from cavity mirror 406 is directed by beamsplitting element 417 through a phasor 420 (or other adjustable light attenuating element) and returns to source 401, via beamsplitting element 413. Optical isolators 418 and 419 are provided to completely block light which travels in the opposite direction. For example, optical isolator element 419 blocks light returning (e.g., reflected light or light escaping from the cavity via mirror 405) from mirror 405 toward source 401 and optical isolator element 418 prevents light returning from phasor 420 (e.g., light reflected by phasor 420 or source light reflected by beamsplitter 413 that is passing through phasor 420 on an opposite path) from impinging on mirror 406. Selection of the cavity mirror reflectivities (e.g., $R_1$ and $R_2$) defines the optical feedback intensity provided to source 401. Use of phasor 420 advantageously allows for phase control of the optical feedback provided to source 401 from the cavity 404. Optional modulator 422 can be provided to modulate the intensity of light travelling to and from source 401, e.g., in a double-pass configuration as shown in FIG. 8b.

Figure 5:
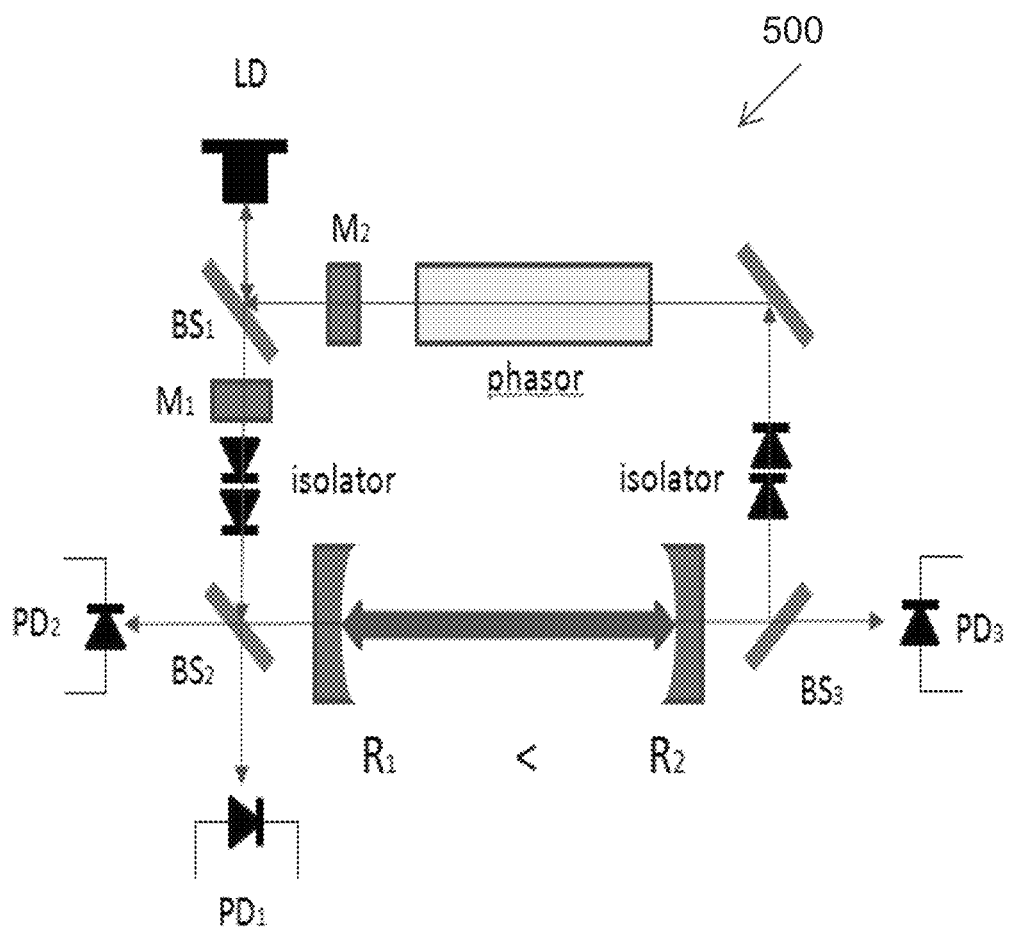

The configuration shown in FIG. 5 is similar to that shown in FIG. 4, but includes a two modulator configuration including modulator $M_1$ and modulator $M_2$, rather than a single modulator. The two modulator configuration is used to stabilize the feedback intensity and reduce any laser disturbance due to modulation as shown in FIG. 8a; modulator $M_1$ modulates the source light impinging on the cavity 404 and modulator $M_2$ (de)modulates the light emerging from the cavity 404 and incident on the laser source 401.

Figure 6:
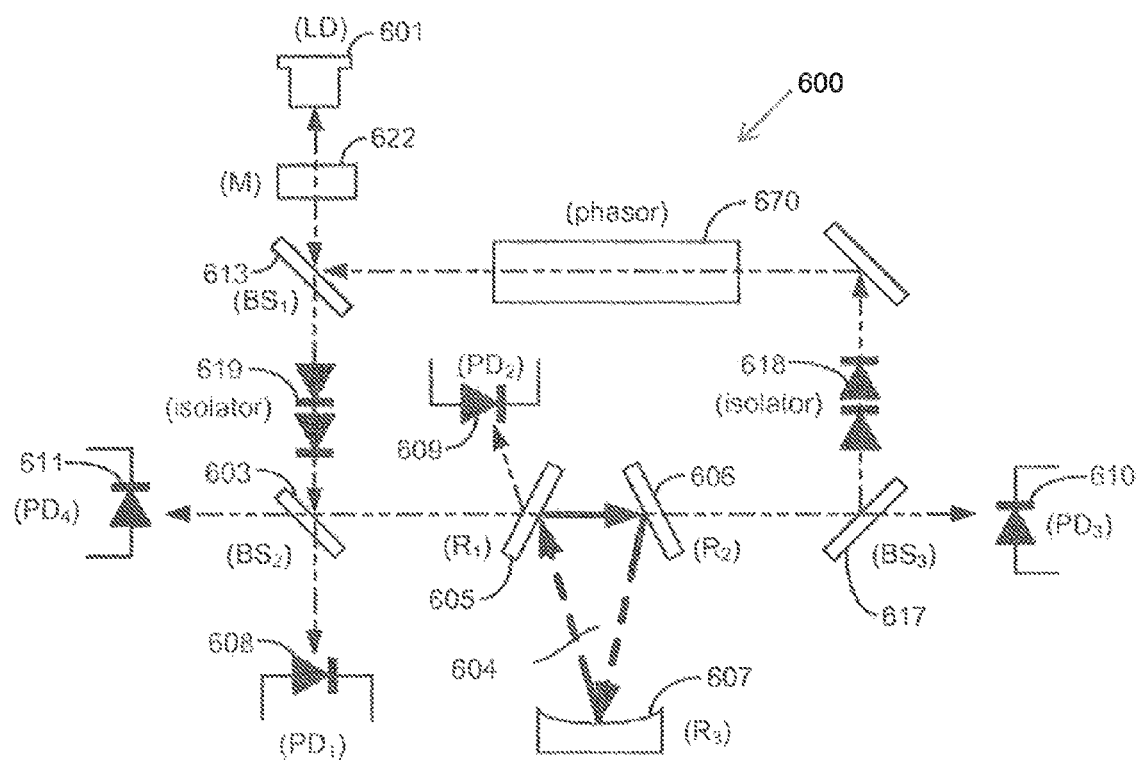

FIG. 6 illustrates a cavity enhanced absorption spectroscopy (CEAS) system 600 according to yet another embodiment. The principle of operation of CEAS system 600 is similar to that of CEAS system 100, for example, but includes a three-mirror ring-shaped cavity structure 604, with cavity mirror 605 being a cavity coupling mirror. More than three mirrors may be used to define the ring cavity. Light circulates within cavity 604 in a unidirectional manner as shown. Cavity coupling mirror 605 is positioned such that incident light beam 612 generated by laser diode source 601 impinges upon mirror 605 at an angle relative to the plane defined by mirror 605 at the area of impact so that light is reflected to photodetector 609. Beamsplitting element 603 allows a portion 613 of incident beam 612 to pass to detector 608 and reflects the remainder to mirror 605. Photodetector 610, in this embodiment, is positioned to receive and detect the portion of the intracavity light 618 circulating within cavity 604 between mirrors 605, 606 and 607 that emerges or escapes via mirror 606. Similar to the operation of CEAS 100, photodetector 608 detects and generates a signal representing the intensity of the laser light 612 incident on the cavity coupling mirror 605, detector 609 detects and generates a signal representing the intensity of the laser light reflected by the cavity coupling mirror 605, and detector 610 detects and generates a signal representing the intracavity optical power of light circulating in the cavity 604. An intelligence module (e.g., processor; not shown) receives the detector output signals and processes these signals to produce or generate a signal that characterizes the cavity loss based on the detection methodology used.

Also shown in FIG. 6 are additional elements to enhance control of the optical feedback, specifically control of the optical feedback to source 601. As shown, a portion of light emerging from cavity mirror 606 is directed by beamsplitting element 617 through a phasor 620 (or other adjustable light attenuating element) and returns to source 601, via beamsplitting element 613.

Optical isolators 618 and 619 are provided to completely block light which travels in the opposite direction. For example, optical isolator element 619 blocks light returning (e.g., reflected light or light escaping from the cavity via mirror 605) from mirror 605 toward source 601 and optical isolator element 618 prevents light returning from phasor 620 (e.g., light reflected by phasor 620 or source light reflected by beamsplitter 613 that is passing through phasor 620 on an opposite path) from impinging on mirror 607. Selection of the cavity mirror reflectivities (e.g., $R_1$, $R_2$ and $R_3$) defines the optical feedback intensity provided to source 601. Use of phasor 620 advantageously allows for phase control of the optical feedback provided to source 601 from the cavity 604.

Additional photodetector 611 is provided to measure, e.g., an intensity of any light circulating backward in the ring cavity. Optional modulator 622 can be provided to modulate the intensity of light travelling to and from source 601, e.g., in a double-pass configuration as shown in FIG. 8b.

Figure 7:
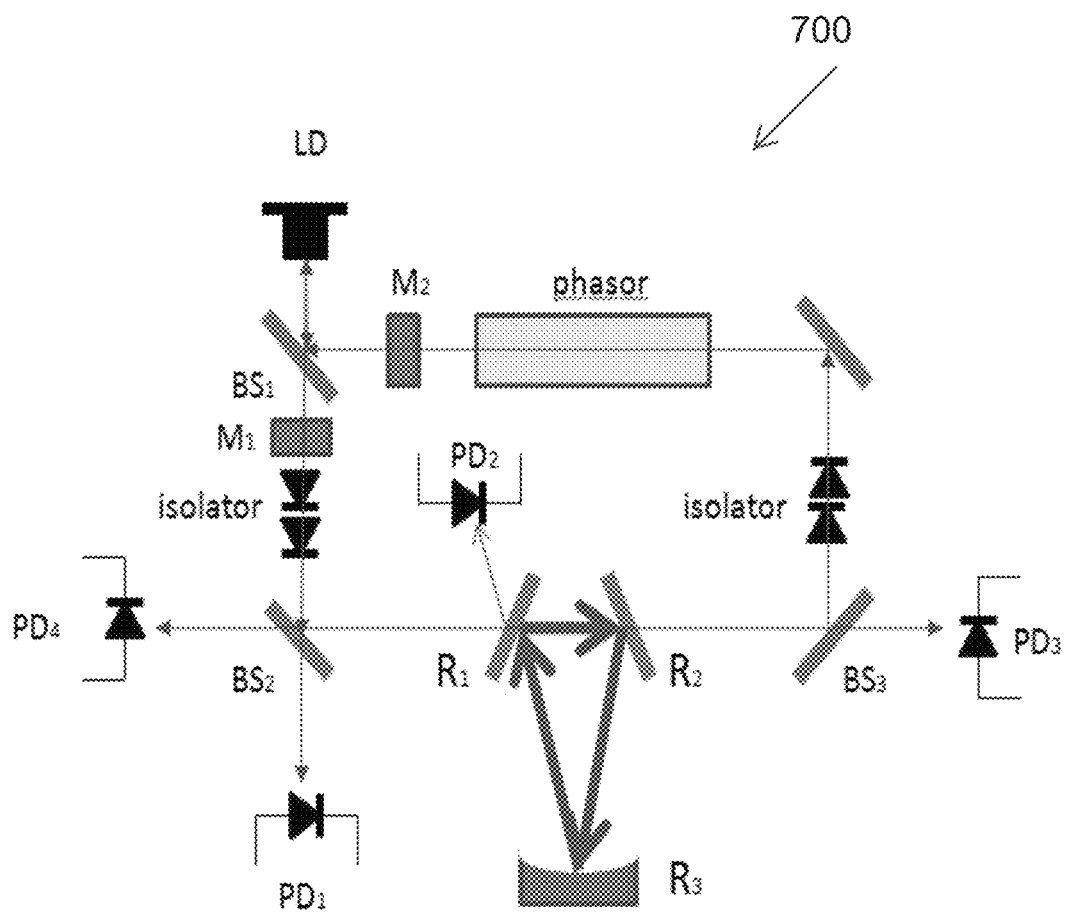

The configuration shown in FIG. 7 is similar to that shown in FIG. 6, but includes a two modulator configuration including modulator $M_1$ and modulator $M_2$. The two modulator configuration is used to stabilize the feedback intensity and reduce any laser disturbance due to modulation as shown in FIG. 8a; modulator $M_1$ modulates the source light impinging on the cavity and modulator $M_2$ (de)modulates the light emerging from the cavity and incident on the laser source.

FIGS. 9-10 shows embodiments of an AOM used in two different double-pass configurations useful for frequency shifting the feedback light back to the original source frequency. Rapid switching from the light injection mode to the decay time measurement mode of an isolated cavity is accomplished by using the same acousto-optic deflector (AOD) in double-pass with +n-th order diffraction in the laser to cavity path, and −n-th order diffraction on the cavity to laser path. This advantageously allows for using the high on/off speed of the AOD and also maintaining the ability to use optical feedback assisted injection by elimination of the AOD optical frequency shift.

Figure 11:
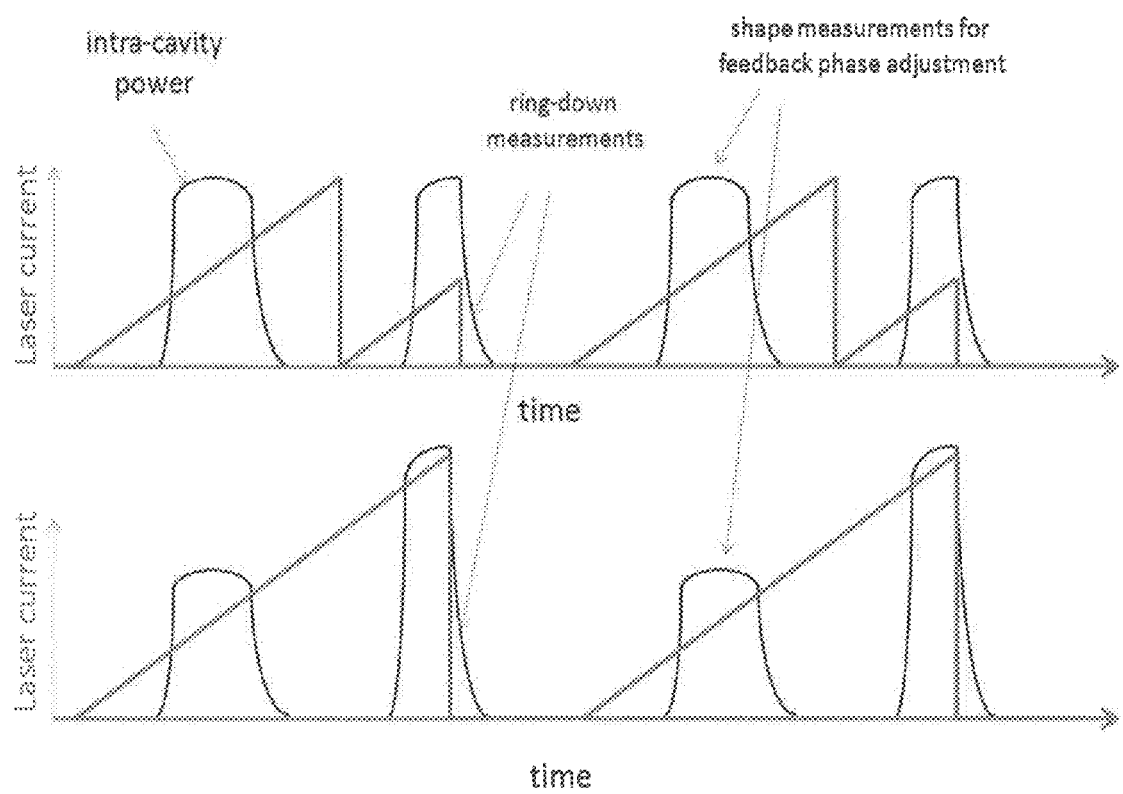
FIG. 11 illustrates two examples of the use of an instrument based on the free decay rate cavity ring down spectroscopy method according to embodiments herein.

FIG. 11 illustrates two examples of the use of an instrument based on the free decay rate cavity ring down spectroscopy method according to embodiments herein. In both examples, the phase of the optical feedback is stabilized by periodic measurements of the time dependence of the intra-cavity power while the laser is scanned through a cavity mode.

Operational Aspects and Advantages

Figure 12:
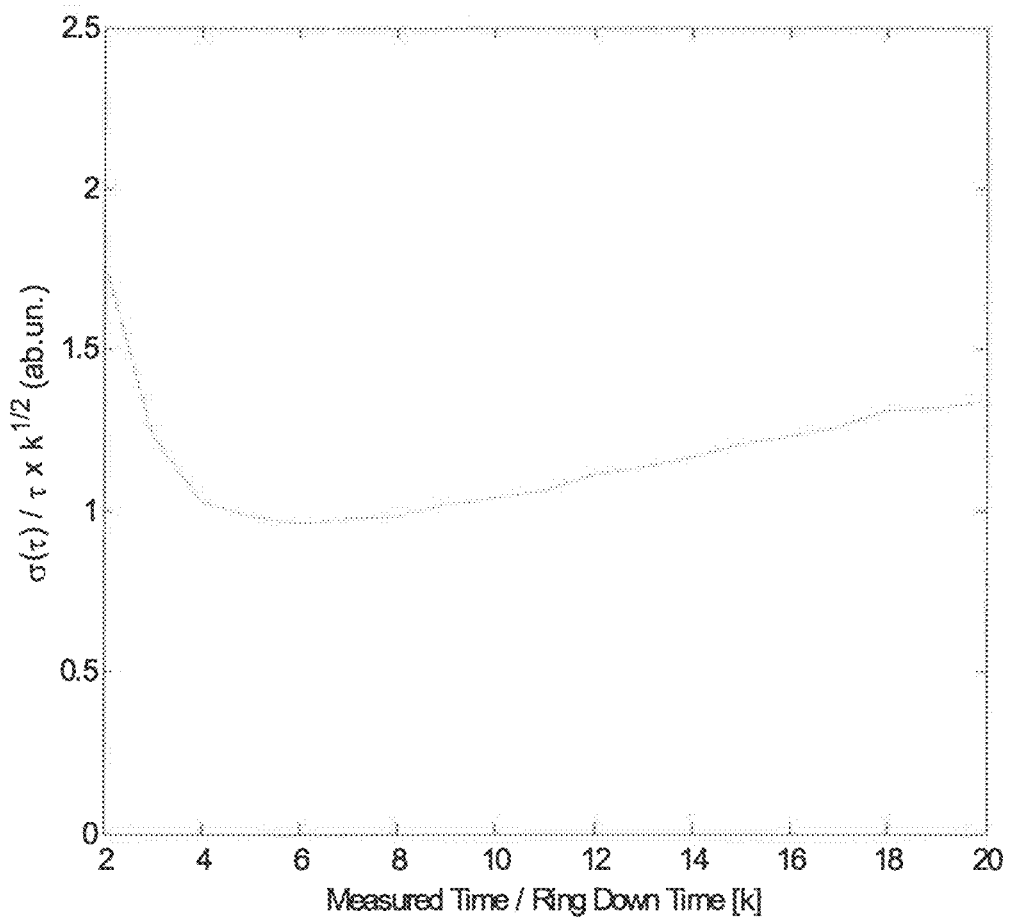
FIG. 12 illustrates a graph indicative of the optimal modulation frequency for the case where a second optical modulator is used to keep the laser locked to the cavity while the cavity is blocked from the laser.

Precision in measurements of the ring-down time in a single event depends in particular on noise level in the photodetector signal. That precision is increased with the increase of the measuring time. However, in practice, if the measurement time exceeds the ring-down time by the factor of 10, the precision will not be further improved. The precision of measuring the ring-down time at particular wavelength is a square-root function of the ring-down repetition rate. Using a second modulator, e.g., as shown in the configurations of FIGS. 3, 5 and 7, advantageously allows for maintaining the laser locked to the cavity while the cavity is blocked from the laser, if the blocking time does not exceed several ring-down times. FIG. 12 shows that in this case the optimal modulation frequency is between 6 and 12 inversed ring-down times.

For CRDS, the laser drive current is typically modulated by a series of square wave pulses or a series of sawtooth pulses generated by control electronics, and the laser is switched off at the negative step of the applied pulse (an example of the latter, sawtooth-shaped, pulses can be found in the bottom portion of FIG. 11) resulting in an exponential decay in intensity in the cavity, which can be measured. Depending on the magnitude and the length of the pulse, one or multiple cavity modes may be excited during that pulse. With appropriate timing of the length of the pulse, the negative step can be made to coincide with an excited cavity mode (e.g., at or near the center peak of the cavity mode), and an exponential decay signal of the cavity is measured as shown in FIG. 11. In one embodiment, the control module turns off the laser, or reduces the applied current below the laser threshold, when the laser locks to a cavity mode and when an intensity of the intracavity optical power of light circulating in the cavity reaches a threshold value or when a difference between the laser frequency and the frequency of the cavity mode reaches a specific value.

According to one embodiment, a methodology to optimize control of the laser output and optimize the repetition rate is provided. In one embodiment, an instrument that implements the method based on free decay rate cavity ring down spectroscopy includes a laser source, an optical cavity (v-shaped, ring cavity, linear cavity, etc), a phasor or other phase adjustment element and a detector. In certain aspects, the instrument includes an attenuator to control the intensity of the optical feedback. However, the system need not have a separate modulator between the laser and the cavity. The laser is periodically turned on and off by modulation of the laser diode current. After the laser is turned on, its frequency tunes to the equilibrium value. The shape of the laser current profile applied is used to tune the laser to a particular cavity mode. When the laser frequency is close to the cavity mode, the laser locks to the cavity mode. When the laser frequency reaches the center of the desired cavity mode, the laser is turned off, and the free decay of the intra-cavity power is measured. The moment when the laser is turned off can be defined by measuring the shape of the intracavity power time dependence. For example, the laser can be turned off when the intracavity power reaches its maximum for a particular cavity mode. The laser diode current in the "off" state should be below the laser threshold, but it can be non-zero. In certain embodiments, the laser is turned off after the derivative of the transmission light signal (e.g., intracavity power signal) has passed its minimum value, but before the derivative reaches its maximum value.

In one embodiment, the shape of laser diode current modulation profile can be optimized to maximize the repetition rate and/or control the order of cavity modes hit or excited. The shape of the applied laser current modulation profile can be preselected or predetermined so as to excite a single desired cavity mode one or multiple consecutive times, or multiple different cavity modes in any particular order as determined based on the shape of the applied current profile. In certain aspects, a periodic correction to the laser diode current shape can be applied based on the cavity, laser aging and other system/device parameters, and the shape of the applied current profile can be corrected or adjusted during a scan.

In one embodiment, for example, the shape of the applied laser diode current can be determined or chosen to actively select one or more particular cavity modes and the order that cavity modes are excited and locked on. For example, the shape of the laser diode current can be optimized or chosen to excite cavity modes in any desired or predetermined order. This is useful for measuring the dynamics of the intracavity optical power on desired cavity mode(s) such as measuring the ring down decay at one particular cavity mode one or multiple consecutive times, or over a continuous set of cavity modes, or over a preselected set of the cavity modes. The order of the modes within a preselected set of modes can be sequential, with all consecutive modes excited and locked on, or it can be sequential, yet non-consecutive, e.g., with one or more distinct modes skipped, or the order within the set can be non-sequential. The shape of the laser current can be chosen to measure ring down decay once or multiple times per cycle for a particular cavity mode, e.g., depending on the importance of that mode in the spectral analysis being conducted.

It should be appreciated that "consecutive" is meant to mean in succession, or in uninterrupted succession, and "sequential" is meant to mean following or subsequent in a regular sequence, but not necessarily successive or consecutive, i.e., there can be interrupted "succession". The following examples will help illustrate the definitions of "consecutive" and "sequential" as used herein. Assuming a full sample set of possible modes as being {1, 2, 3, 4, 5, 6, 7, 8, 9, 10}:

A) A consecutive set might include {1, 2, 3, 4, 5, 6, 7, 8, 9, 10}, {3, 4, 5, 6}, {1, 2, 3, 4}, or {4, 5, 6, 7, 8, 9}, etc. so long as all elements in the set are successive (uninterrupted succession within that set). Note, all these sets are also sequential, i.e., each element follows, or is subsequent in order from the previous element in the set.

B) A non-consecutive set would include {1, 2, 3, 4, 7, 8, 9, 10}, {3, 5, 6, 8}, {1, 5, 9}, etc, as here the elements in the set are not successive. All these sets are also sequential—there is interruption in the sequence, yet each element is subsequent in order.

C) A non-consecutive set could also include {1, 5, 3, 9, 7}, {1, 2, 3, 8, 7, 6, 10}, {1, 2, 4, 3, 6, 5, 7, 8, 9, 10} or {3, 1, 2, 4, 5, 6}, etc. Here also, the sets are non-sequential as not all elements are subsequent to the previous element or do not follow in a regular sequence.

D) A consecutive set could also include {10, 9, 8, 7, 6, 5, 4, 3, 2, 1}, or {8, 7, 6, 5, 4}. These sets would also be sequential, since they follow in a regular sequence.

E) A non-consecutive set could include {10, 9, 8, 7, 4, 3, 2, 1}, or {8, 7, 5, 4}. These sets would also be sequential.

When the laser is turned "off" (is set below the laser threshold value), the laser medium cools down and loses heat. This lost heat may impact the repetition rate as extra time may be required to reestablish equilibrium when the laser is turned back on. In one embodiment, the applied current profile includes a shape that compensates for heat lost in the laser medium when the laser is turned off or is set to below the lasing threshold. In this manner, control of the repetition rate, how soon the next mode is hit and/or the order in which modes are excited is optimized. The amount of heat lost can be determined based on how long the laser was below threshold (and the applied current and laser diode voltage if non-zero) or turned "off". If the amount of heat lost is known, a compensation pulse portion can be applied to add back in some or all of the lost heat so as to compensate for the lost heat. In one embodiment, the laser is driven below its maximum allowed current during normal operation. After the laser is turned "off" (e.g., to perform a decay rate measurement at an excited mode) at the end of one pulse, a compensation pulse portion of the next pulse is applied wherein the laser is turned on up to its maximum allowed drive current for a duration or period of time, $\Delta t$, that compensates for some or all of the amount of heat lost when the laser was in the off state (or below threshold). The current is then dropped back down to a desired level and the current ramp continued. The heat lost, and also the heat to be added, can be determined from the equation: $P*\Delta t = I_{LD}*V_{LD}$ or $P=(I_{LD}*V_{LD})/\Delta t$, where I and V are the current and voltage of the laser diode and $\Delta t$ is the time of the applied pulse portion (or time in the "off" state for determining lost heat). In this manner, when the laser hits the next cavity mode can be controlled, e.g., the laser can be controlled so that the laser hits the next cavity mode at the same place (in time) during a scan as it would have had the laser not been turned off to make a decay measurement. Controlling the shape of the current pulses applied to the laser in this manner advantageously allows for accessing cavity modes with a higher repetition rate.

In one embodiment, at least one cavity mode is non-interrupted during a scan; this means when the laser frequency is scanned, the laser locks consecutively to different cavity modes, and for at least one cavity mode, which has the same transverse mode structure as modes used for ring-down measurements, the laser is not turned "off" while it is locked to this cavity mode. In certain aspects, this mode of operation is useful for the laser phase adjustment.

Figure 13:
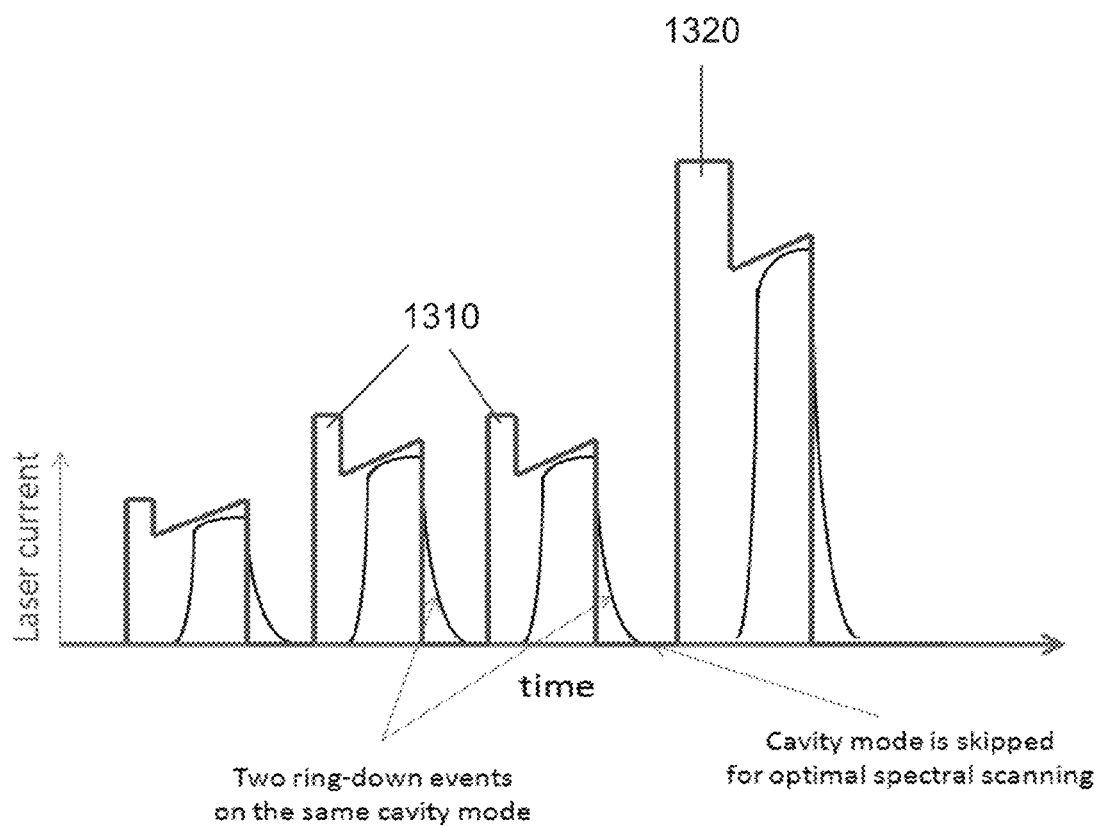
FIG. 13 illustrates an example of laser control whereby the laser is repeatedly locked to the same cavity mode and then jumps to another cavity mode, skipping one or more intermediary cavity modes according to one embodiment.

FIG. 13 illustrates an example of laser control using an applied laser current modulation profile whereby during an excitation cycle the laser is controlled to repeatedly (twice in this example) lock to the same cavity mode and then jump to another cavity mode, skipping one or more intermediary cavity modes, according to one embodiment. As can be seen, the applied current profile, including compensation pulse portions 1310 and 1320, advantageously control the cavity modes excited/hit and/or the order in which the modes are hit. In this example, a cavity mode is purposefully skipped.

Figure 14:
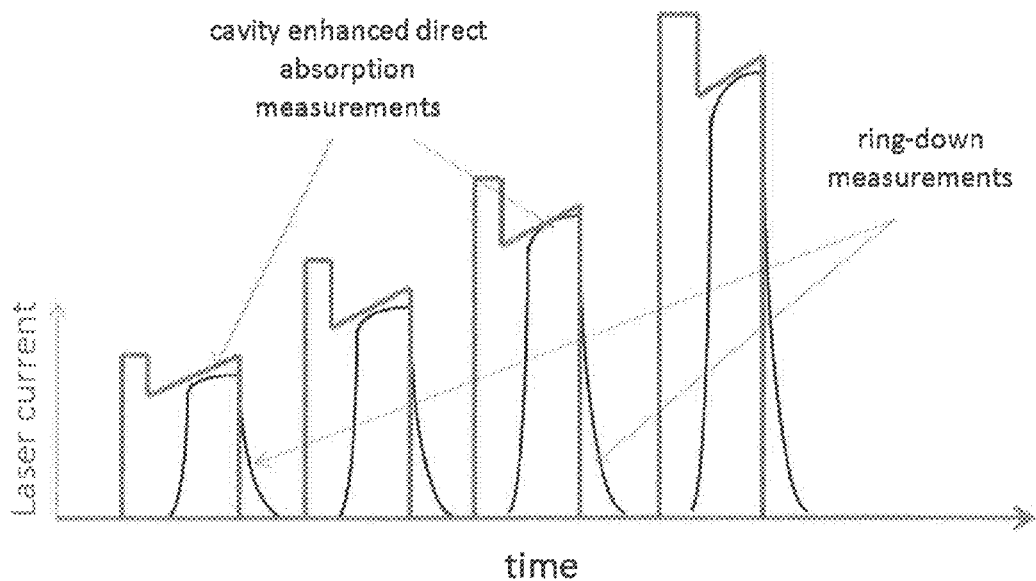
FIG. 14 illustrates an example of laser control whereby both cavity enhanced direct absorption and free decay rate measurement methods are used in the same excitation cycle according to one embodiment.

FIG. 14 illustrates an example of laser control using an applied laser current modulation profile whereby during an excitation cycle the laser is controlled to lock to sequential (and adjacent) cavity modes. In this example, both decay rate measurements and direct absorption measurements are taken during the same cycle at the times shown. As can be seen, in certain embodiments, when scanning between two consecutively measured cavity modes n and m, the laser current compensation portion exceeds the values if the current In and Im, where In and Im are the laser current values when the laser was turned "off" to measure cavity losses at the n-th and m-th cavity modes, respectively.

Figure 15:
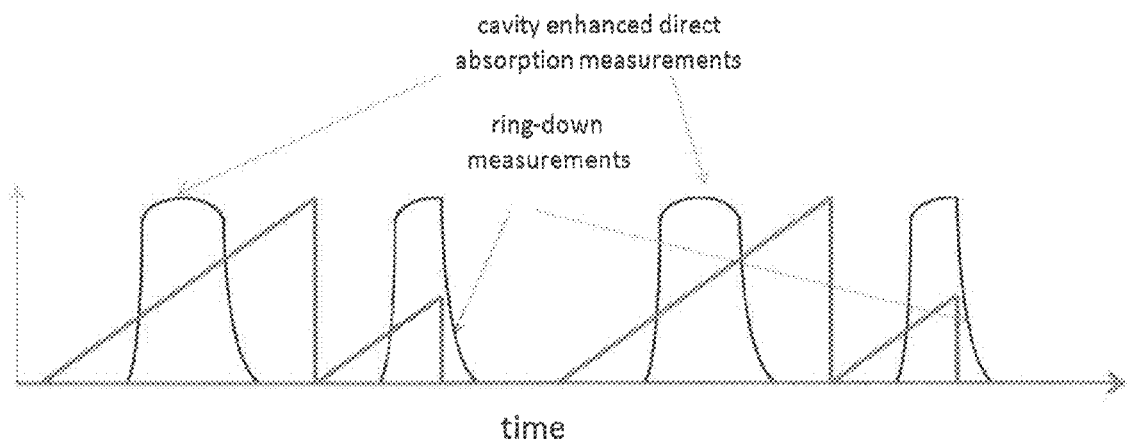
FIG. 15 illustrates an example of laser control whereby both cavity enhanced direct absorption and free decay rate measurement methods are used in the different excitation cycles according to one embodiment.

FIG. 15 illustrates an example of laser control using an applied laser current modulation profile whereby during an excitation cycle the laser is controlled to lock to the same cavity mode multiple times. In this example, both cavity enhanced direct absorption and free decay rate measurement methods are used in the different excitation.

Figure 16:
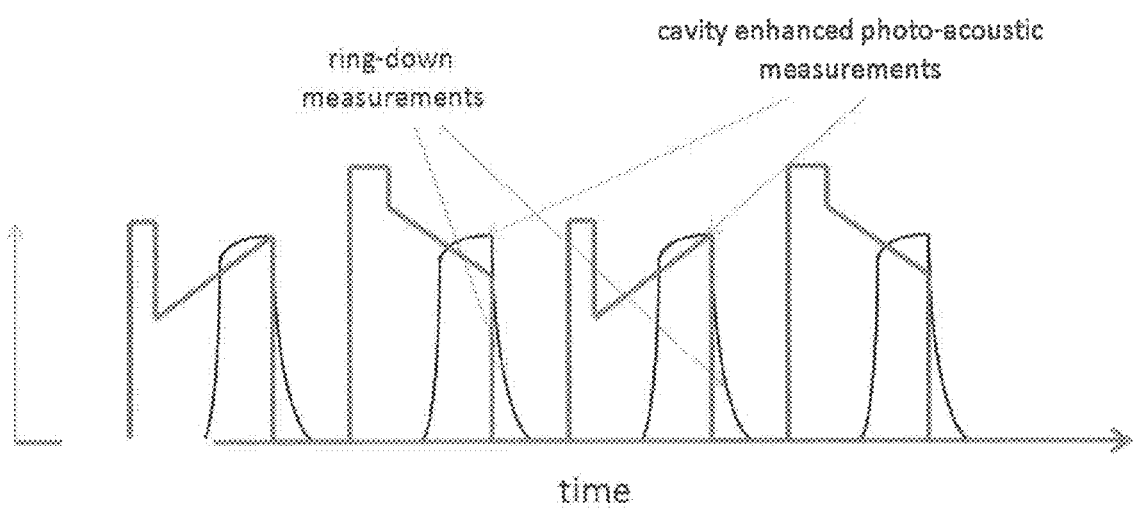
FIG. 16 shows another example of laser control whereby both cavity enhanced and free decay rate measurement methods are used in the same excitation cycle according to one embodiment.

FIG. 16 shows another example of laser control using an applied laser current modulation profile whereby during an excitation cycle the laser is controlled to lock to the same cavity mode multiple times. In this example, both cavity enhanced and free decay rate measurement methods are used in the same excitation cycle. As can be seen here, the current ramp after the compensation pulse portion can include a negative ramp to facilitate optimal control of the modes excited.

Figure 17:
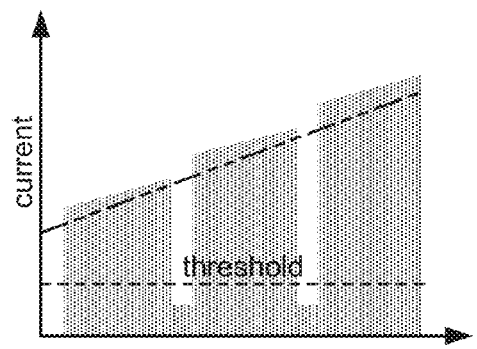
FIG. 17 illustrates examples of applied current pulses that compensate for heat lost when the laser is turned "off".
Figure 17:
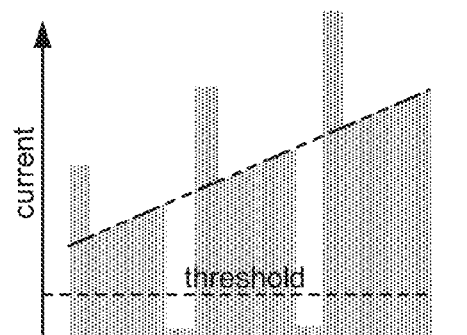
Figure 17:
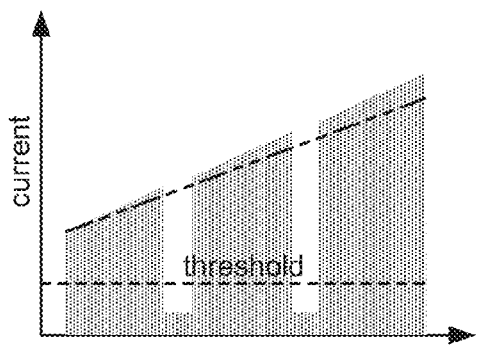

FIG. 17 illustrates examples of applied current pulses that compensate for heat lost when the laser is turned "off". In these examples, the "off" state of the laser is shown as being below the laser threshold, but having a non-zero value. For comparison, the "optimal" laser current scan is also shown; the optimal laser scan represents the case where consecutive modes are hit when the laser is not turned "off". The dash-dot lines are the optimal current profiles for scans without laser interruption. The optimal current profile represents the highest scanning rate, or close to it, while the instantaneous spectral distribution of the intra-cavity light is narrower than the cavity resonances. In all three cases there is a part in laser current profile that is above the optimal current profile.

In certain aspects, the phase of the optical feedback is stabilized by periodic measurements of the time dependence of the intra-cavity power while the laser is scanned through a cavity mode, or by other methods. Because the cavity is not completely blocked from the laser, when the laser is off (e.g., below threshold), the laser and the cavity create a system of two coupled cavities. In that case, the decay time in the optical cavity not only depends on the intra-cavity loss, but also depends on the coupling between two cavities. However, because the optical length of both cavities is fixed (the laser-cavity optical path is controlled by the phasor), the frequencies of the cavities are also fixed. Hence, the shot-to-shot performance is not affected by incomplete blocking of the laser from the cavity, if the phase of the optical feedback is controlled. Additional spectral fringes caused by interference of an optical element placed between the laser and the cavity can be measured by periodic measurement of the cavity loss without absorbing species present in the cavity.

In one embodiment, a ring down decay measurement can be taken at any point during a pulse (cavity mode excitation). In this embodiment, the first pulse is used to measure the phase of the laser, and subsequent pulses are then used for decay measurements, e.g., the laser turned off, or set to below threshold, and a decay rate measured. The first mode excited is used as a tracker for determining how well the conditions for OF to the laser are fulfilled, and what adjustments may need to be made. In this manner, for subsequent pulses, the decay rate measurements can be taken at any time during the pulse, e.g., at a point before or after the maximum of the pulse where there is sufficient intensity to make a reasonable measurement. Additionally, this technique facilitates more rapid measurements, e.g., on the order of 3 KHz repetition rate for a 30 µs ring-down time, than are possible in conventional cavity ring down measurement techniques, e.g., on the order of 300 Hz measurement rate.

Miscellaneous

As used herein, the terms "threshold intensity value" or "threshold value" or "threshold" when used with reference to a laser source and to optical feedback of the laser source is intended to mean the intensity of the optical feedback above which the laser will lock to a cavity mode for one FSR (free spectral range) of the cavity. Two examples show the condition when the optical feedback strength is above the threshold value: 1) when a cavity mode is scanned for more than one FSR, but the laser continues to be locked to the same cavity mode; 2) when the laser current or temperature of the laser is adjusted so that the laser frequency is scanned, and when unperturbed by optical feedback the laser frequency would be scanned for more than one cavity FSR, whereas in the presence of the (high) optical feedback the laser continues to be locked to the same cavity mode. As above, it is desirable in cavity enhanced absorption systems and methods to avoid this situation, and indeed the above embodiments advantageously ensure that the laser locks to desired cavity modes as the laser wavelength is being controlled.

As described above, the various embodiments described herein advantageously provide methods, systems and apparatus for precise determination of trace gas concentrations with further improved stability and reproducibility as compared to existing devices and methods based upon various detection schemes of cavity enhanced spectroscopy. The various embodiments advantageously provide higher immunity to variations of ambient conditions while retaining or improving other parameters such as the measurement repetition rate, measurement precision, low power consumption and low cost.

The various embodiments disclosed herein offer some or all of the following advantages:

Increased accuracy of the cavity loss measurement by determining the decay constant of the radiation trapped in the cavity is achieved by making this decay purely exponential. This is accomplished by total isolation of the cavity from any optical coupling with external elements during the decay measurement, e.g., by introduction of optical isolators into an optical path between the cavity and the photodetectors, and by rapid interruption of the optical path between the laser and the cavity within the fraction of the decay time in the beginning of the decay time measurement cycle.

Improved measurement precision is achieved by using optical feedback between the cavity and the laser source at the stage of injecting the radiation into the cavity, thus permitting to reduce the time interval between subsequent measurements to several decay times.

Additional improvement of the decay time measurement accuracy is obtained because of high monochromaticity of the radiation injected by optical feedback leading to purely exponential decay.

Much lower device cost is made possible due to the ability to use low power laser diodes in the simplest packages due to the very high efficiency of the radiation injection by optical feedback.

Simple and reliable laser source control is provided by special cavity excitation sequence that comprises sequential excitation of at least two cavity modes where the last excited mode is used for decay time measurement, whereas the preceding mode excitation curve is used to maintain the correct value of the optical feedback phase.

Additional simplification and reduction of price is achieved by using the cavity mode structure itself in combination with the cavity mode grid position versus measured absorption peak as an extremely precise wavelength calibration tool, thus avoiding the need of wavelength monitor.

Rapid switch from the light injection mode to the decay time measurement mode of the isolated cavity is accomplished by using the same acousto-optic deflector (AOD) in double-pass with +n-th order diffraction in the laser-to-cavity path, and −n-th order diffraction on the cavity-to-laser path. This permits one to take advantage of the high on/off speed of the AOD and still be able to use optical feedback assisted injection by elimination of the AOD optical frequency shift.

Additional benefits of the above embodiments include the following, and others:

Improved stability, precision, and reproducibility of the measurements of trace gas concentrations.

Longer periods between device or instrument calibrations.

Lower complexity of the device by elimination of such components as ultra-high accuracy wavelength monitor.

Much lower price of the laser components needed in the device resulting in its reduced cost.

Increased reliability and robustness of the device due to using simpler control algorithms.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of measuring cavity loss of a resonant optical cavity over a range of frequencies by exciting one or a plurality of cavity modes of the cavity in a controlled manner, the cavity having at least two cavity mirrors, one of which is a cavity coupling mirror, using a laser that emits continuous wave laser light, wherein the laser is responsive to optical feedback light emerging from the cavity, and wherein a mean optical frequency of the laser is adjustable over a range of frequencies, the method comprising:

coupling the laser light to the cavity via the cavity coupling mirror using mode matching optics, the cavity having a plurality of optical resonance cavity modes that have frequencies within said range of frequencies of the laser;

applying to the laser a drive current comprising a series of current pulses, each having a predetermined current profile, so as to adjust the mean optical frequency of the laser and to excite desired cavity modes in an order as determined based on the shape of the applied current pulses; and detecting dynamics of the intra cavity optical power of light circulating in the cavity after a cavity mode has been excited, wherein an end portion of one current pulse sets the laser drive current below a laser threshold value, wherein the current profile of the next current pulse applied to the laser includes a compensation pulse portion that drives the laser at a current level and for a duration sufficient to compensate for some or all of the laser heat lost while the laser drive current was below the laser threshold value and to excite the next mode in said order.

2. The method of claim 1, wherein said order is a non-sequential order.

3. The method of claim 1, wherein said order is a sequential order with at least one mode skipped.

4. The method of claim 3, wherein detecting dynamics includes measuring a free decay rate cavity ring down event.

5. The method of claim 3, wherein the cavity has a configuration selected from the group consisting of a ring cavity having three or more cavity mirrors and a linear cavity having two or more cavity mirrors.

6. The method of claim 1, further comprising determining a concentration of a gas in the cavity responsive to detecting dynamics of the intra cavity optical power.

7. The method of claim 1, wherein said current level is at or near a maximum laser driving current.

8. A system for measuring cavity loss of a resonant optical cavity over a range of frequencies by exciting one or a plurality of cavity modes of the cavity, the system comprising:

a resonant optical cavity having at least two cavity mirrors, one of which is a cavity coupling mirror, the cavity having a plurality of optical resonance cavity modes;

a laser that emits continuous wave laser light, wherein the laser is capable of being scanned whereby a mean optical frequency of the laser is adjustable over a range of frequencies, and wherein the laser is responsive to optical feedback light emerging from the cavity, and wherein the modes of the cavity have frequencies within said range of frequencies of the laser;

mode matching optics configured to couple the laser light to the cavity via the cavity coupling mirror;

a control module coupled with the laser and adapted to apply a drive current comprising a series of current pulses, each pulse having a predetermined current profile, to the laser so as to adjust the mean optical frequency of the laser and to excite desired cavity modes in an excitation order as determined based on the shape of the applied current pulses; and a first detector configured to measure dynamics of the intra cavity optical power of light circulating in the cavity after a cavity mode has been excited, wherein an end portion of one current pulse sets the laser drive current below a laser threshold value, and wherein the current profile of the next current pulse applied to the laser includes a compensation pulse portion that drives the laser at a current level and for a duration sufficient to compensate for some or all of the laser heat lost while the laser current was below the laser threshold value and to excite the next mode in said excitation order.

9. The system of claim 8, wherein said order is a non-sequential order.

10. The system of claim 8, wherein, said order is a sequential order with at least one mode skipped.

11. The system of claim 8, wherein the first detector is configured to measure a free decay rate cavity ring down event.

12. The system of claim 8, wherein the cavity has a configuration selected from the group consisting of a ring cavity having three or more cavity mirrors and a linear cavity having two or more cavity mirrors.

13. The system of claim 8, further including a processor adapted to determine a concentration of a gas in the cavity responsive to a signal received from the first detector.

14. The method of claim 8, wherein said current level is at or near a maximum laser driving current.

15. A gas analyzer for detecting one or more analyte species present in a gaseous or liquid medium, the gas analyzer comprising:

a resonant optical cavity having at least two cavity mirrors, one of which is a cavity coupling mirror, the cavity having a plurality of optical resonance cavity modes;

a laser that emits continuous wave laser light, wherein the laser is capable of being scanned whereby a mean optical frequency of the laser is adjustable over a range of frequencies, and wherein the laser is responsive to optical feedback light emerging from the cavity, and wherein the modes of the cavity have frequencies within said range of frequencies of the laser;

mode matching optics configured to couple the laser light to the cavity via the cavity coupling mirror;

a control module coupled with the laser and adapted to apply a drive current comprising a series of current pulses, each pulse having a predetermined current profile, to the laser so as to adjust the mean optical frequency of the laser and to excite desired cavity modes in an excitation order as determined based on the shape of the applied current pulses;

a first detector configured to measure dynamics of the intra cavity optical power of light circulating in the cavity after a cavity mode has been excited, wherein an end portion of one current pulse sets the laser drive current below a laser threshold value, wherein the current profile of the next current pulse applied to the laser includes a compensation pulse portion that drives the laser at a current level and for a duration sufficient to compensate for some or all of the laser heat lost while the laser current was below the laser threshold value and to excite the next mode in said excitation order; and a processor adapted to determine a concentration of an analyte species in the cavity responsive to a signal received from the first detector.

* * * * *